United States Patent [19]

Ishiyama et al.

[11] Patent Number: 5,756,822
[45] Date of Patent: May 26, 1998

[54] AMINOETHANETHIOL DERIVATIVE

[75] Inventors: Nobuo Ishiyama; Toshihiro Koyama; Mitsuo Hayashida; Katsuyuki Otsuka; Masahiro Fujii; Kunio Kimura; Yoshiyuki Hata; Nobuko Miyao, all of Kyoto, Japan

[73] Assignee: Kaken Pharmaceutical Co., Ltd., Tokyo, Japan

[21] Appl. No.: 833,132

[22] Filed: Apr. 4, 1997

Related U.S. Application Data

[62] Division of Ser. No. 424,500, PCT/JP93/01696, filed Nov. 18, 1993, Pat. No. 5,672,597.

Foreign Application Priority Data

Nov. 20, 1992 [JP] Japan ................. 4-312184
Apr. 27, 1993 [JP] Japan ................. 5-100804

[51] Int. Cl.$^6$ ................................ C07C 69/00
[52] U.S. Cl. .................. 560/130; 560/145; 560/147; 560/150; 560/170; 560/179
[58] Field of Search ................. 560/130, 145, 560/147, 150, 155, 170, 179

[56] References Cited

U.S. PATENT DOCUMENTS

| | | | |
|---|---|---|---|
| 3,840,543 | 10/1974 | Kanai et al. | 514/927 |
| 3,862,176 | 1/1975 | Fauran et al. | 514/927 |
| 3,910,932 | 10/1975 | Cavalla et al. | 514/929 |
| 3,950,542 | 4/1976 | Kalopissis et al. | 424/316 |
| 4,297,357 | 10/1981 | Miki et al. | 514/349 |
| 4,299,974 | 11/1981 | Liu et al. | 560/148 |
| 4,439,444 | 3/1984 | Nisato et al. | 514/927 |
| 4,521,417 | 6/1985 | Nakamoto et al. | 514/255 |
| 4,912,101 | 3/1990 | Hirakawa et al. | 514/210 |
| 4,916,233 | 4/1990 | Ueno et al. | 548/342 |
| 4,950,667 | 8/1990 | Mitsumori et al. | 514/341 |
| 4,977,267 | 12/1990 | Hirakawa et al. | 546/272 |
| 5,177,223 | 1/1993 | Arai et al. | 546/201 |
| 5,192,774 | 3/1993 | Shinozaki et al. | 514/331 |
| 5,317,026 | 5/1994 | Otagiri et al. | 514/331 |
| 5,319,143 | 6/1994 | Messersmith et al. | 564/500 |

FOREIGN PATENT DOCUMENTS

| | | |
|---|---|---|
| 0 282 077 | 9/1988 | European Pat. Off. . |
| 319644 | 6/1989 | European Pat. Off. . |
| 59-45650 | 11/1984 | Japan . |
| 63-225371 | 9/1988 | Japan . |

OTHER PUBLICATIONS

Chemical Abstracts, vol. 92, No. 12, Abstract No. 103527f, p. 636, Mar. 24, 1980.

*Primary Examiner*—Randy Gulakowski
*Attorney, Agent, or Firm*—Armstrong, Westerman, Hattori, McLeland & Naughton

[57] ABSTRACT

An acetamide derivative having the general formula (I):

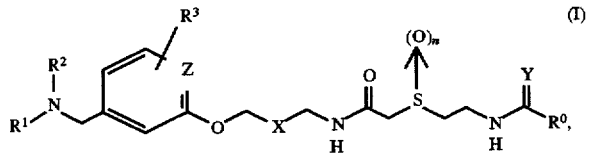

or a pharmacologically acceptable salt thereof; a synthetic intermediate of the above-mentioned acetamide derivative; a treating agent for peptic ulcer and for gastritis which comprises the above-mentioned compound having the general formula (I) as an effective ingredient, and a process for treating peptic ulcer and gastritis using the above-mentioned compound having the general formula (I), are disclosed.

1 Claim, No Drawings

AMINOETHANETHIOL DERIVATIVE

This is a division of application Ser. No. 08/424,500 filed May 18, 1995, now Pat. No. 5,612,597 which is a § 371 national phase of international application PCT/JP 93/01696 filed Nov. 18, 1993.

TECHNICAL FIELD

The present invention, which relates to a novel acetamide derivative having both of an inhibition of gastric acid secretion and a potentiation of defensive factor, is a useful invention in the medicinal field.

BACKGROUND ART

Peptic ulcer occurs owing to ill-balance between offensive factors such as gastric acid and pepsin, and defensive factors such as gastric mucus and mucosal blood flow. In particular, gastric acid is considered to take part in it importantly. Therefore, there are now widely used offensive factor inhibitors, for example, histamine $H_2$-receptor blockers having particularly potent inhibition of gastric acid secretion, such as cimetidine and famotidine. However, there is a problem in the use of histamine $H_2$-receptor blockers such as recrudescence or relapse of the ulcer after breaking the use thereof. It is considered that such problem occurs mainly due to defensive factors such as gastric mucosa, which are weakened by the potent inhibition of gastric acid secretion. So, there has been desired the development of a medicament having both of an inhibition of gastric acid secretion and a potentiation of defensive factor. As such medicaments, there are described, for example, compounds having pyridine ring in Japanese Unexamined Patent Publication No. 225371/1988, U.S. Pat. No. 4912101 and U.S. Pat. No. 4977267. However, there has not yet been known any compound which satisfactorily possesses both of the above-mentioned inhibition of gastric acid secretion and potentiation of defensive factor.

The object of the present invention is to provide a novel compound effective for preventing and treating peptic ulcer and gastritis, which not only has both of potent inhibition of gastric acid secretion and potentiation of defensive factor, but also has an accelerating effect for curing chronic ulcer.

DISCLOSURE OF THE INVENTION

Acetamide derivatives of the present invention are an acetamide derivative having the general formula (I):

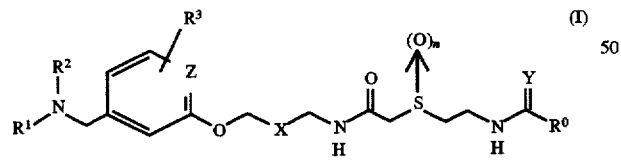

wherein each of $R^1$ and $R^2$ is a $C_{1-7}$ alkyl group, or $R^1$ and $R^2$ together form the formula —$(CH_2)_m$— wherein m is 4 to 6, $R^3$ is hydrogen atom, a halogen atom, a $C_{1-7}$ alkyl group, a $C_{1-4}$ alkoxy group, nitro group, amino group, cyano group, carboxyl group or acetyl group, which may be substituted for any hydrogen atom of the ring, X is —$CH_2$— or —CH=CH—, n is 0 or 1, Y is oxygen atom, sulfur atom or =N—CN, Z is CH or nitrogen atom, and $R^0$ is $R^4$, —$NHR^5$ or —$OR^6$, wherein each of $R^4$, $R^5$ and $R^6$ is hydrogen atom; a $C_{1-7}$ alkyl group; a $C_{2-6}$ alkenyl group; a $C_{2-6}$ alkynyl group; a $C_{1-4}$ alkoxy $C_{1-7}$ alkyl group; a $C_{1-5}$ acyloxy C1-7 alkyl group; a $C_{7-16}$ aralkyl group; a phenyl or a heterocyclic group which may be substituted by a $C_{1-7}$ alkyl group, a halogen atom, a $C_{1-4}$ alkoxy group, nitro group, trifluoromethyl group, amino group, cyano group, carboxyl group or acetyl group; a $C_{1-7}$ alkyl group substituted by a heterocycle, or a pharmacologically acceptable salt thereof and an acetamide derivative, which is a synthetic intermediate of the above-mentioned acetamide derivative, having the general formula (VIII):

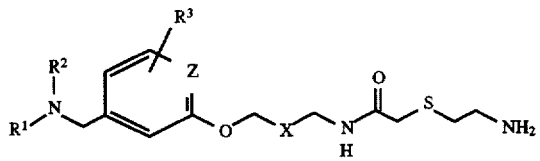

wherein each of $R^1$ and $R^2$ is a $C_{1-7}$ alkyl group, or $R^1$ and $R^2$ together form the formula —$(CH_2)_m$— wherein m is 4 to 6, $R_3$ is hydrogen atom, a halogen atom a $C_{1-7}$ alkyl group, a $C_{1-4}$ alkoxy group, nitro group, amino group, cyano group, carboxyl group or acetyl group, which may be substituted for any hydrogen atom of the ring, X is —$CH_2$— or —CH=CH—, and Z is CH or nitrogen atom.

The present invention also relates to an aminoethanethiol derivative having the general formula (XX):

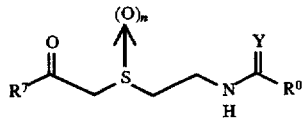

wherein $R^7$ is hydroxyl group, a $C_{1-7}$ alkoxy group, or a phenoxy group which may be substituted, n is 0 or 1, Y is oxygen atom, sulfur atom or =N—CN, and $R_0$ is $R^4$, —$NHR^5$ or —$OR^6$, wherein each of $R^4$, $R_5$ and $R^6$ is hydrogen atom; a $C_{1-7}$ alkyl group; a $C_{1-6}$ alkenyl group; a $C_{2-6}$ alkynyl group; a $C_{1-4}$ alkoxy $C_{1-7}$ alkyl group; a $C_{1-5}$ acyloxy $C_{1-7}$ alkyl group; a $C_{7-16}$ aralkyl group; a phenyl or a heterocyclic group which may be substituted by a $C_{1-7}$ alkyl group, a halogen atom, a $C_{1-4}$ alkoxy group, nitro group, trifluoromethyl group, amino group, cyano group, carboxyl group or acetyl group; a $C_{1-7}$ alkyl group substituted by a heterocycle, a treating agent for peptic ulcer and a treating agent for gastritis, both of which comprises the above-mentioned compound having the general formula (I) or a salt thereof as an effective ingredient, and a method for treating peptic ulcer and gastritis using the above-mentioned compound having the general formula (I) or a salt thereof.

According to the present invention, there is provided a novel acetamide derivative having the general formula (I), which has the excellent curing activity for peptic ulcer and for gastritis.

The compound having the general formula (I) of the present invention shows a potent anti-ulcer effect in a test of ulcer induced by pylorus-ligation, which ulcer is induced mainly due to gastric acid etc., in a test of ulcer induced by hydrochloric acid/ethanol, which ulcer is induced mainly due to defensive factors such as mucosal blood flow and mucus, and in a test of ulcer induced by a stress of restraint plus water-immersion, which ulcer is due to both of offensive and defensive factors. Thus the above-mentioned compound has been proved to act on both of the main factors in ulcer. Further, the compound has an activity of improving gastric mucosal blood flow and shows an accelerating effect for curing chronic ulcer induced by acetic acid. Thus the compound has been proved useful as a medicament for treatment and prevention of recrudescence or relapse, of acute or chronic gastric ulcer, duodenal ulcer and gastritis. The treating agent in the present invention also includes preventive treatment.

The present invention also provides a useful intermediate for synthesizing the compound having the general formula (I).

In the general formulae (I), (VIII) and (XX), a $C_{1-7}$ alkyl group, represented by $R^1$, $R^2$, $R^3$, $R^4$, $R^5$, $R^6$ and a substituent of phenyl group or a heterocycle, means a straight, branched or cyclic $C_{1-7}$ alkyl group, for example, methyl group, ethyl group, n-propyl group, n-butyl group, n-pentyl group, n-hexyl group, isopropyl group, isobutyl group, sec-butyl group, t-butyl group, cyclopropyl group, cyclobutyl group, cyclopentyl group, cyclohexyl group, cycloheptyl group, and the like.

A halogen atom represented by $R^3$ and a substituent of phenyl group or a heterocycle, is fluorine atom, chlorine atom, bromine atom or iodine atom. A $C_{1-4}$ alkoxy group means a straight, branched or cyclic $C_{1-4}$ alkoxy group, for example, methoxy group, ethoxy group, n-propoxy group, n-butoxy group, isopropoxy group, isobutoxy group, sec-butoxy group, t-butoxy group, cyclopropoxy group, cyclobutoxy group and the like.

A $C_{2-6}$ alkenyl group represented by $R^4$, $R^5$ and $R^6$ means a straight, branched or cyclic $C_{2-6}$ alkenyl group, for example, vinyl group, allyl group, butenyl group and the like.

A $C_{2-6}$ alkynyl group means a straight, branched or cyclic $C_{2-6}$ alkynyl group, for example, ethynyl group, propynyl group and the like.

A $C_{1-4}$ alkoxy $C_{1-7}$ alkyl group means a group wherein a straight, branched or cyclic $C_{1-4}$ alkoxy group is bound to a straight, branched or cyclic $C_{1-7}$ alkyl group, for example, methoxymethyl group, methoxyethyl group, ethoxyethyl group and the like.

A $C_{1-5}$ acyloxy $C_{1-7}$ alkyl group means a group wherein a straight or branched $C_{1-5}$ acyloxy group is bound to a straight, branched or cyclic $C_{1-7}$ alkyl group, for example, formyloxymethyl group, acetoxymethyl group, propoxymethyl group, acetoxyethyl group and the like.

A $C_{7-16}$ aralkyl group means a group wherein a $C_{6-10}$ aryl group is bound to a straight, branched or cyclic $C_{1-6}$ alkyl group, for example, benzyl group, phenethyl group, naphthylmethyl group and the like.

Further, a heterocyclic group is, for example, furyl group, 2-nitrofuryl group, 2-cyanofuryl group, 2-methylfuryl group, thienyl group, pyrrolyl group, imidazolyl group, triazolyl group, tetrazolyl group, thiazolyl group, pyridyl group, pyrazinyl group, quinolyl group, isoquinolyl group and the like.

A $C_{1-7}$ alkyl group substituted by a heterocycle means a group wherein the above-mentioned heterocycle is bound to a straight, branched or cyclic $C_{1-7}$ alkyl group, for example, thenyl group, furfuryl group, pyrrolyimethyl group and the like.

A $C_{1-7}$ alkoxy group represented by $R_7$ means a straight or branched $C_{1-7}$ alkoxy group, for example, methoxy group, ethoxy group, n-propoxy group, n-butoxy group, isopropoxy group, isobutoxy group, sec-butoxy group, t-butoxy group, n-hexyloxy group and the like. A phenoxy group which may be substituted is, for example, pentafluorophenoxy group, 4-nitrophenoxy group and the like.

The present invention also includes a pharmacologically acceptable salt of the acetamide derivative having the general formula (I). As such salts, there are, for example, a salt with a hydrohalogenic acid such as hydrofluoric acid, hydrochloric acid, hydrobromic acid or hydroiodic acid; a salt with an inorganic acid such as nitric acid, perchloric acid, sulfuric acid, phosphoric acid or carbonic acid; a salt with a lower alkyl sulfonic acid such as methanesulfonic acid, trifluoromethanesulfonic acid or ethanesulfonic acid; a salt with an arylsulfonic acid such as benzenesulfonic acid or p-toluenesulfonic acid; a salt with an organic acid such as fumaric acid, succinic acid, citric acid, tartaric acid, oxalic acid or maleic acid; a salt with an amino acid such as glycine, alanine, glutamic acid or aspartic acid; a salt with an aromatic carboxylic acid such as benzoic acid, salicyclic acid, hibensoic acid, fendizoic acid, naphthoic acid, hydroxynaphthoic acid or pamoic acid; and the like.

The acetamide derivative of the present invention having the general formula (I) can be prepared, for example, as follows:

Process A The compound having the general formula (I) can be obtained by condensing a compound having the general formula (II):

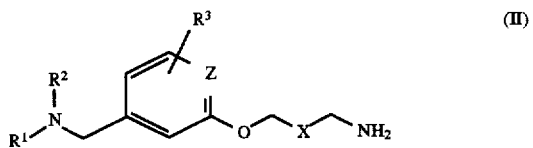

(II)

and a compound having the general formula (III):

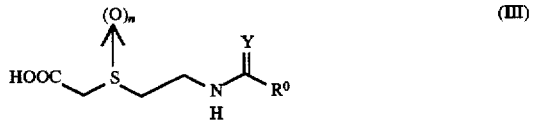

(III)

wherein $R^1$, $R^2$, $R^3$, $R^0$, X, Y, Z and n are the same as defined above.

The reaction of the compound having the general formula (II) and the compound having the general formula (III) should be carried out in the presence of a condensing agent. As the condensing agent, dicyclohexylcarbodiimide (hereinafter, referred to as DCC), 1-ethyl-3-(dimethylaminopropyl)carbodiimide hydrochloride (hereinafter, referred to as WSC), or the like can be used alone or together with 1-hydroxy-1H-benzotriazole monohydrate (hereinafter, referred to as HOBt). In the reaction, generally, there is preferably used an inert solvent, for example, a halogenated hydrocarbon such as dichloromethane or chloroform, an aromatic hydrocarbon such as benzene, toluene or xylene, an ether such as tetrahydrofuran or dioxane, an amide such as dimethylformamide or dimethylacetamide, acetonitrile, dimethyl sulfoxide and the like.

The reaction temperature and reaction time can be varied according to the compounds used as a raw material. Generally, it is desirable to carry out the reaction at a temperature of 0° C. to reflux temperature, for a reaction time of 30 minutes to 18 hours.

The compound having the general formula (III) used herein can be prepared, for example, as follows:

2-Aminoethanethiol and compounds having the

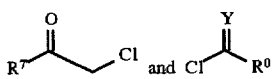

to give a compound having the general formula (XXa):

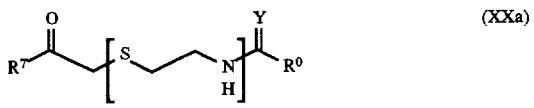

(XXa)

wherein $R^0$ and Y are the same as defined above, and $R^7$ is a $C_{1-7}$ alkoxy group. Further, the oxidation thereof can bring about a compound having the general formula (XXb):

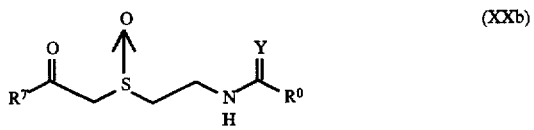

(XXb)

wherein $R^0$, $R^7$ and Y are the same as defined above. Thus obtained compound having the general formula (XXa) or (XXb) is hydrolyzed to give the compound having the general formula (III). These aminoethanethiol derivatives having the general formula (XX):

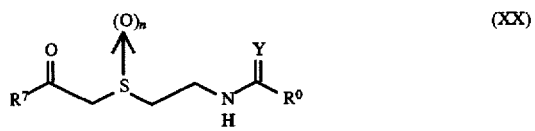

(XX)

wherein $R^7$, n, Y and $R^0$ are the same as defined above, are useful synthetic intermediates for preparing the acetamide derivative having the general formula (I) of the present invention.

Process B The compound having the general formula (I) can be obtained by reacting the compound having the general formula (II):

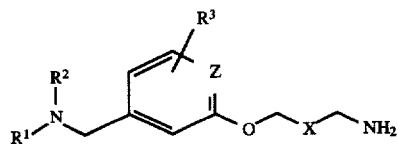

(II)

and a compound having the general formula (IV):

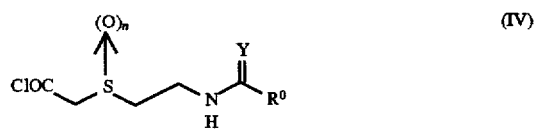

(IV)

wherein $R_1$, $R_2$, $R_3$, $R_4$, $R_0$, X, Y, Z and n are the same as defined above.

The reaction of the compound having the general formula (II) and the compound having the general formula (IV) is desirably carried out in a solvent which does not influence the reaction. As the solvent, there can be used a halogenated hydrocarbon such as dichloromethane or chloroform, an aromatic hydrocarbon such as benzene, toluene or Etylene, an ether such as tetrahydrofuran or dioxane, an amide such as dimethylformamide or dimethylacetamide, acetonitrile, dimethyl sulfoxide and the like.

It is desirable to carry out the reaction at a reaction temperature of 0° to 50° C., for a reaction time of 30 minutes to 18 hours. An organic base or an inorganic base is used as a dehalogenating agent. However, the reaction can be also carried out in the absence of any base in the above-mentioned solvent.

Process C

A compound having the general formula (V) can be reacted with a compound having the general formula (VI) to give a compound having the general formula (VII) which is a compound having the general formula (I) wherein n=0, as follows:

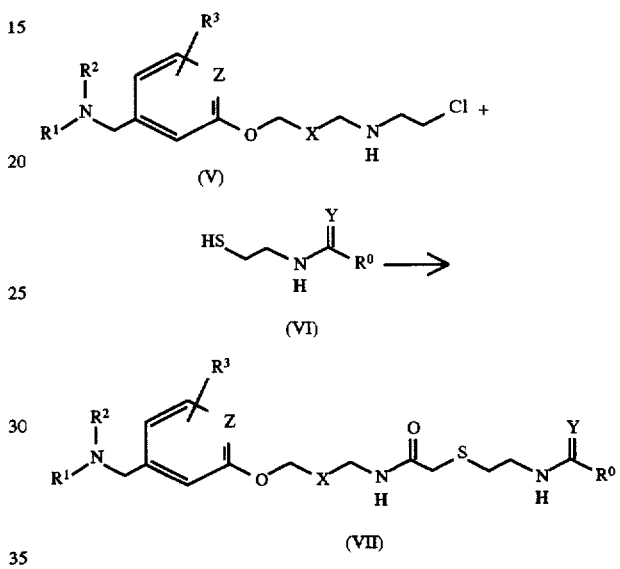

wherein $R^1$, $R^2$, $R^3$, $R^0$, X, Y and Z are the same as defined above.

The reaction of the compound having the general formula (V) and the compound having the general formula (VI) is desirably carried out in a solvent which does not influence the reaction. As the solvent, there can be used an alcohol such as methanol, ethanol or propanol, a halogenated hydrocarbon such as dichloromethane or chloroform, an aromatic hydrocarbon such as benzene, toluene or xylene, an ether such as tetrahydrofuran or dioxane, an amide such as dimethylformamide or dimethylacetamide, acetonitrile, dimethyl sulfoxide and the like.

It is desirable to carry out the reaction at a reaction temperature of 0° to 50° C., for a reaction time of 30 minutes to 18 hours. An organic base or an inorganic base is preferably used as a dehalogenating agent.

Process D

Also, the compound having the general formula (I) of the present invention can be easily prepared from the compound having the general formula (VIII) which can be obtained by reacting the compound having the general formula (V) and 2-aminoethanethiol, as shown below. That is, the compound having the general formula (VIII) is a useful intermediate for synthesizing the compound having the general formula (I). The present invention also provides such a synthetic intermediate.

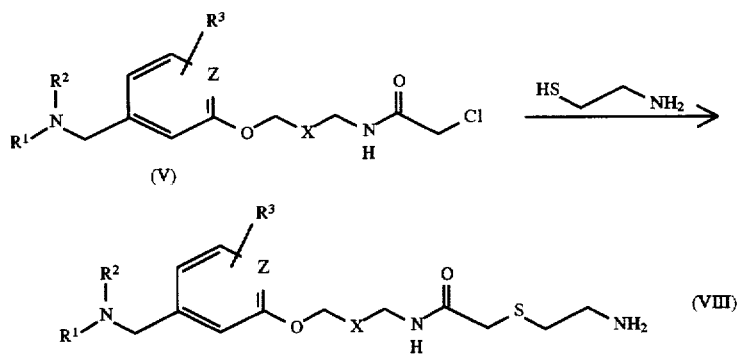

wherein $R^1$, $R^2$, $R^3$, X and Z are the same as defined above.

The compound having the general formula (VIII) can be reacted with a compound having the general formula (IX), (XI), (XII), (XIV), (XVI) or (XVIII) to give a compound having the general formula (X), (XIII) or (XV) which is the compound having the general formula (I) wherein $R^0$ is $R^4$, —$OR^6$ or —$NHR^5$ and Y is oxygen atom; a compound having the general formula (XVII) which is the compound (I) wherein $R^0$ is —$NHR^5$ and Y is sulfur atom; or a compound having the general formula (XIX) which is the compound (I) wherein $R^0$ is $R^4$ and Y is =NCN.

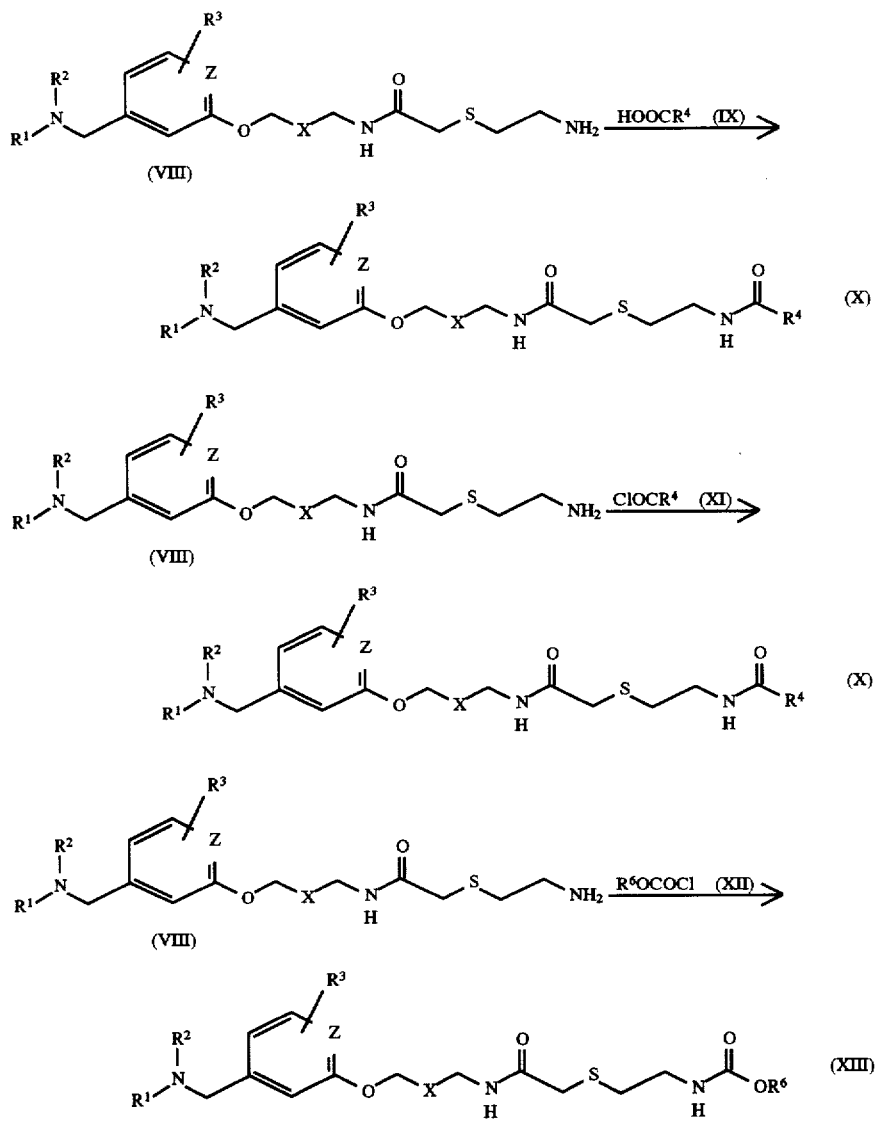

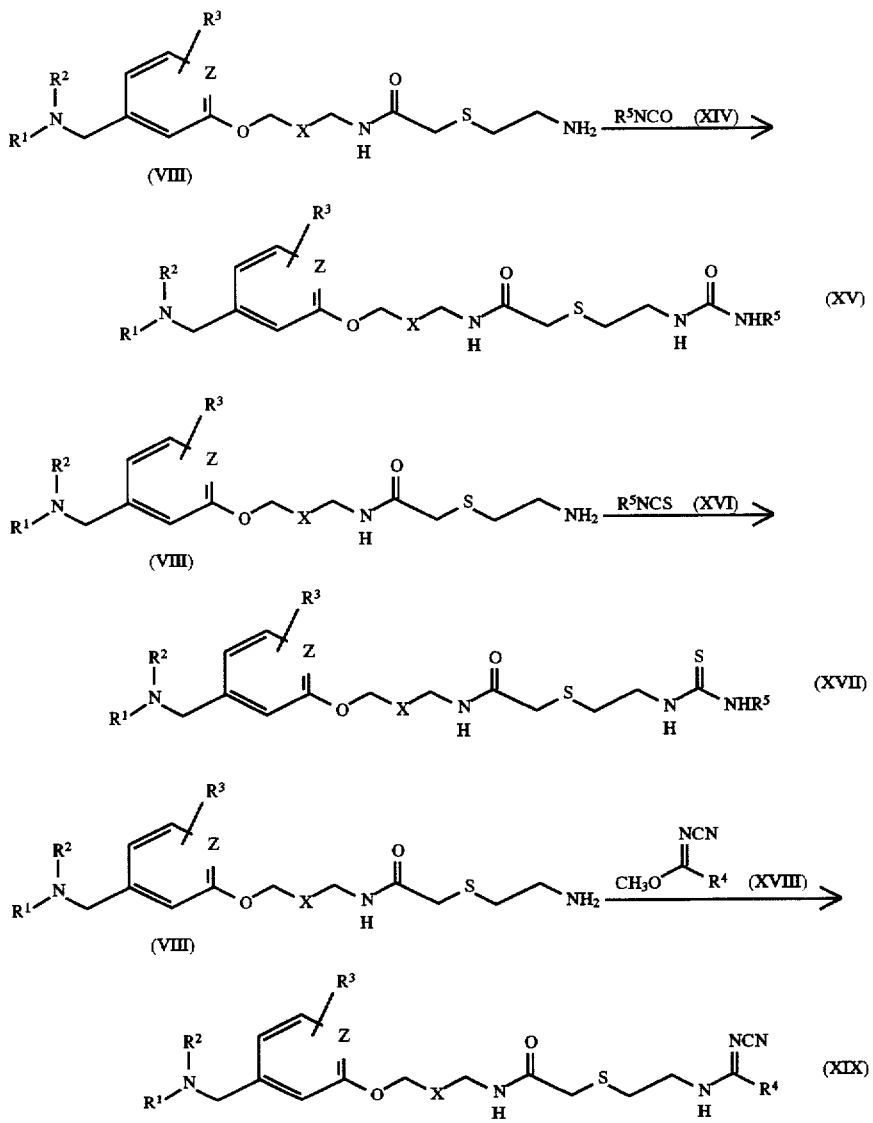

wherein $R_1$, $R_2$, $R_3$, $R_4$, $R_5$, $R_6$, X and Z are the same as defined above.

The reaction of the compound having the general formula (V) and 2-aminoethanethiol is desirably carried out in a solvent which does not influence the reaction. As the solvent, there can be used an alcohol such as methanol, ethanol or propanoi, a halogenated hydrocarbon such as dichloromethane or chloroform, an aromatic hydrocarbon such as benzene, toluene or xylene an ether such as tetrahydrofuran or dioxane, an amide such as dimethylformamide or dimethylacetamide, acetonitrile, dimethyl sulfoxide and the like.

It is desirable to carry out the reaction at a reaction temperature of 0° C. to reflux temperature, for a reaction time of 30 minutes to 18 hours. An organic base or an inorganic base is preferably used as a dehalogenating agent.

The reaction of the compound having the general formula (VIII) and the compound having the general formula (IX) should be carried out in the presence of a condensing agent. As the condensing agent, DCC, WSC or the like can be used alone or together with HOBt. In the reaction, generally, there is preferably used an inert solvent, for example, a halogenated hydrocarbon such as dichloromethane or chloroform, an aromatic hydrocarbon such as benzene, toluene or xylene, an ether such as tetrahydrofuran or dioxane, an amide such as dimethylformamide or dimethylacetamide, acetonitrile, dimethyl sulfoxide and the like.

The reaction temperature and the reaction time can be varied according to the compounds used as a raw material. Generally, it is preferable to carry out the reaction at a temperature of 0° C. to reflux temperature, for a reaction time of 30 minutes to 24 hours.

The reaction of the compound having the general formula (VIII) and the compound having the general formula (XI) or (XII) is desirably carried out in a solvent which does not influence the reaction. As the solvent, there can be used an alcohol such as methanol, ethanol or propanol, a halogenated hydrocarbon such as dichloromethane or chloroform, an aromatic hydrocarbon such as benzene, toluene or xylene, an ether such as tetrahydrofuran or dioxane, an amide such as dimethylformamide or dimethylacetamide, acetonitrile, dimethyl sulfoxide and the like.

It is desirable to carry out the reaction at a reaction temperature of 0° to 50° C. , for a reaction time of 30 minutes to 18 hours. An organic base or an inorganic base is used as a dehalogenating agent. However, the reaction can be also carried out in the absence of any base in the above-mentioned solvent.

The reaction of the compound having the general formula (VIII) and the compound having the general formula (XIV) or (XVI) is desirably carried out in a solvent which does not influence the reaction. As the solvent, there can be used an alcohol such as methanol, ethanol or propanol, a halogenated hydrocarbon such as dichlorometnane or chloroform, an aromatic hydrocarbon such as benzene, toluene or xylene, an ether such as tetrahydrofuran or dioxane, an amide such as dimethylformamide or dimethylacetamide, acetonitrile, dimethyl sulfoxide and the like.

It is preferable to carry out the reaction at a reaction temperature of 0° C. to reflux temperature, for a reaction time of 30 minutes to 18 hours.

The reaction of the compound having the general formula (VIII) and the compound having the general formula (XVIII) is desirably carried out in a solvent which does not influence the reaction. As the solvent, there can be used an alcohol such as methanol, ethanol or propanol, a halogenated hydrocarbon such as dichloromethane or chloroform, an aromatic hydrocarbon such as benzene, toluene or xylene, an ether such as tetrahydrofuran or dioxane, an amide such as dimethylformamide or dimethylacetamide, acetonitrile, dimethyl sulfoxide and the like.

It is preferable to carry out the reaction at a reaction temperature of 0° C. to reflux temperature, for a reaction time of 30 minutes to 18 hours.

In the above-mentioned reactions, any substance which generally acts as a base can be exemplified without any limitation, for the base to be used as an dehalogenating agent. As an organic base, there are, for example, triethylamine, diisopropylethylamine, tributylamine, N-methylmorpholine, N,N-dimethylaniline, N,N-diethylaniline, pyridine, 4-(N,N-dimethyl-amino)pyridine, 1,5-diazabicyclo[4,3,0]non-5-ene, 1,4-diazabicyclo[2,2,2] octane (DABCO), 1,8-diazabicyclo-[5,4,0]undec-7-ene (DBU) and the like. As an inorganic base, there are, for example, an alkali metal carbonate such as sodium carbonate or potassium carbonate, an alkali metal hydrogencarbonate such as sodium hydrogencarbonate or potassium hydrogencarbonate, an alkali metal hydroxide such as sodium hydroxide or barium hydroxide, and the like.

Any acetamide derivative of the present invention having the formula (I) has an excellent inhibition of gastric acid secretion based on the histamine $H_2$-receptor antagonism, together with a potentiation of defensive factor. Further, the above-mentioned acetamide derivative also has an accelerating effect for curing chronic ulcer. Thus, the acetamide derivative can be suitably used for treatment of peptic ulcer and gastritis.

The above-mentioned compound can be administered in itself alone or in various pharmaceutical preparation forms according to known pharmaceutical preparation process using known pharmaceutical additives such as an excipient, a binder and a lubricant. For example, the treating agent for peptic ulcer and the treating agent for gastritis of the present invention can be used as oral pharmaceutical preparation such as tablet, powder, granule, capsule or syrup, or as parenteral pharmaceutical preparation such as injection or suppository.

Although the dosage is different according to the symptom, age or body weight of a patient, treatment effect, or method or period of administration, a suitable dosage is generally 10 to 2000 mg in case of oral administration per day for adults.

BEST MODE FOR CARRYING OUT THE INVENTION

The compound of the present invention and the preparation process thereof are more specifically explained by means of the following Examples. However, it is to be understood that the present invention is not limited to those Examples. In each Example, melting points were determined with Yanagimoto Seisakusho micro melting point measuring apparatus MP-500D. $^1$H-NMR spectra were recorded with Nippon Denshi JNM-EX270 spectrometer. MS were obtained with Shimazu GCMS-QP1000EX instrument. All melting points were uncorrected value.

EXAMPLE 1

N-[3-[3-(piperidinomethyl) phenoxy]propyl]-2-[2-(2-furoylamino)ethylsulfinyl]acetamide

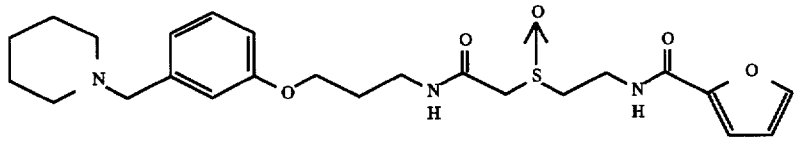

The compound having the general formula (VIII), (X), (XIII), (XV), (XVII) or (XIX) can be led to the compound having the general formula (I) by oxidation.

These oxidations are desirably carried out in a solvent which does not influence the reaction.

As the solvent, there can be used an alcohol such as methanol, ethanol or propanol, a halogenated hydrocarbon such as dichloromethane or chloroform, an aromatic hydrocarbon such as benzene, toluene or xylene, an ether such as tetrahydrofuran or dioxane, an amide such as dimethylformamide or dimethylacetamide, acetonitrile, dimethyl sulfoxide and the like.

As an oxidizing agent, there can be used periodic acid, hydrogen peroxide, m-chloroperbenzoic acid, perphthalic acid, permaleic acid and the like. The reaction temperature and the reaction time can be varied according to the compounds used as a raw material. Generally, it is preferable to carry out the reaction at a temperature of 0° C. to reflux temperature, for a reaction time of 30 minutes to 24 hours.

There was suspended 3.0 g (0.0122 mol) of 2-[2-(2-furoylamino)ethylsulfinyl)acetic acid inl 100 ml of dichloromethane and added 1.87 g (0.0122 mol) of HOBt and 2.52 g (0.0122 mol) of DCC under cooling with ice, and the mixture was stirred for 30 minutes under cooling with ice. Thereto was added 3.04 g (0.0122 mol) of N-3-[3-(piperidinomethyl)phenoxy]propylamine, and the mixture was stirred for 18 hours at room temperature. The precipitate was filtrated off, and the filtrate was washed with 5 % aqueous solution of sodium hydroxide and with water and dried over Glauber's salt. Then the solvent was removed under reduced pressure and the residue was purified by silica gel column chromatography (chloroform:methanol=5:1) to give 3.0 g of the titled compound as crystals.

m.p.:101.2°–102.5°C.; MS(m/z):475(M$^+$); $^1$H-NMR (CDCl$_3$)δ: 1.43(2H, m), 1.55(4H, m), 1.98(2H, t), 2.36(4H, br), 3.11(1H, m), 3.19(1H, m), 3.41(2H, s), 3.46(2H, m), 3.56(1H, d), 3.73(1H, d), 3.84(2H, m), 3.99(2H, t), 6.44(1H, dd), 6.75(1H, dd), 6.86(1H, d) , 6.89(1H, s), 7.08(1H, d) , 7.17(1H, t), 7.42(1H, s), 7.58(1H, t) , 7.65(1H, t)

There was dissolved 2.0 g of the obtained crystals in 20 ml of ethanol, and 4 ml of 10% solution of hydrochloric acid in ethanol was added thereto, and then removed under reduced pressure to give 2.1 g of hydrochloride thereof as powder.

EXAMPLE 2

N-[3-[3-(piperidinomethyl)phenoxy]propyl]-2-[2-(2-thienylacetamino)ethylthiol]acetamide

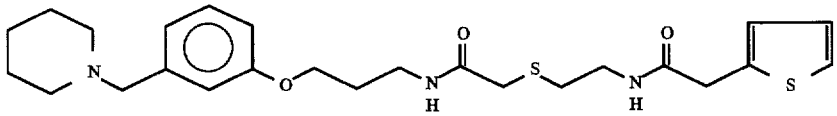

There were dissolved 3.0 g (0.0083 mol) of N-[3-[3-(piperidinomethyl)phenoxy]propyl]-2-chloroacetamide and 1.67 g (0.0083 mol) of N-(2-mercaptoethyl)-2-thienylacetamide in 4 0 ml of ethanol. Thereto was added a solution of 0.93 g (0.0166 mol) of potassium hydroxide in 10 ml of ethanol and the mixture was refluxed with heating for 18 hours. The precipitate was filtrated off, and the filtrate was removed under reduced pressure. The residue was dissolved in ethyl acetate and washed with saturated aqueous solution of sodium chloride and dried over Glauber's salt. Then the solvent was removed under reduced pressure. The residue was purified by silica gel column chromatography (chloroform:ethanol=5:1) to give 0.48 g of the titled compound as crystals.

m.p.:90.1°–92.1° C.; MS(m/z):489(M$^+$); $^1$H-NMR (CDCl$_3$)δ: 1.43(2H, m), 1.57(4H, m), 2.01(2H, m), 2.38(4H, m) , 2.64(2H, m), 3.19(2H, m), 3.44(2H, s), 3.47(4H, m), 3.72(2H, s), 4.05(2H, t), 6.34(1H, br), 6.80(1H, dd), 6.94 (4H, m), 7.22(3H, m)

According to the same manner as in Example 1 hydrochloride thereof was prepared.

EXAMPLE 3

N-[3-[3-(piperidinomethyl)phenoxy]propyl]-2-[2-(2-thienylacetamino)ethylsulfinyl]acetamide

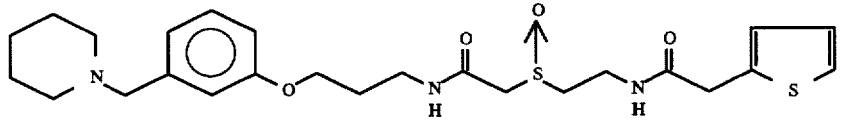

There was dissolved 1.0 g (0.002 mol) of N-[3-[3-(piperidinomethyl)phenoxy]propyl]-2-[2-(2-thienylacetamino)ethylthio]acetamide in 30 ml of acetic acid and added 0.24 ml (0.0022 mol) of 30 % aqueous solution of hydrogen peroxide under cooling with ice, and the mixture was stirred for 12 hours at room temperature. The solvent was removed under reduced pressure, and then the residue was purified by silica gel column chromatography (chloroform:ethanol=5:1) to give 0.72 g of the titled compound as crystals.

m.p.:103.8°–105.5° C.; MS(m/z):505(M$^+$); $^1$H-NMR (CDCl$_3$)δ: 1.46(2H, m) 1.62(4H, m), 1.98(2H, m), 2.51(4H, br), 3.03(2H, m), 3.58(10H, m), 3.99(2H, t), 6.80(1H, d), 6.90(4H, m), 7.19(2H, m), 7.50(1H, m), 7.77(1H, m)

According to the same manner as in Example 1 hydrochloride thereof was prepared.

EXAMPLE 4

N-[4-[(2-methoxy-5-piperidinomethyl) phenoxy]cis-2-butenyl]-2-[2-(3-furoylamino)ethylthio]acetamide

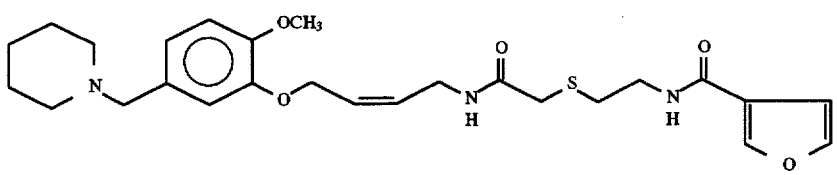

There was suspended 3.16 g (0.0138 mol) of 2-[(3-furoylamino)ethylthio]acetic acid in 100 mg of dichloromethane and added 2.1 g (0.0138 mol) of HOBt and 2.84 g (0.0138 mol) of DCC under cooling with ice, and the mixture was stirred for 30 minutes under cooling with ice. Thereto was added 4.0 g (0.0138 mol) of 4-[(2-methoxy-2-piperidinomethyl)phenoxy]-cis-2-butenylamine and the mixture was stirred for 18 hours at room temperature. The precipitate was filtrated off, and the filtrate was washed with 5% aqueous solution of sodium hydroxide and with water and dried over Glauber's salt. Then the solvent was removed under reduced pressure and the residue was purified by silica gel column chromatography (chloroform:methanol=5:1) to give 2.2 g of the titled compound as crystals.

m.p.:100.2°–101.5° C.; MS(m/z):501(M$^+$); $_1$H-NMR (CDCl$_3$)δ: 1.43(2H, m), 1.57(4H, m), 2.3 7(4H, br), 2.80 (2H, t), 3.23(2H, s), 3.41(2H, s), 3.62(2H, m), 3.86(3H, s), 3.99(2H, t), 4.57(2H, d), 5.78(1H, m) 5.92(1H, m), 6.73(1H, s), 6.83(1H, s), 6.84(1H, d), 6.92(1H, s), 7.03(1H, br), 7.27(1H, br), 7.40(1H, s), 8.00(1H, s)

According to the same manner as in Example 1 hydrochloride thereof was prepared.

EXAMPLE 5

N-[3-[3-(piperidinomethyl)phenoxy]propyl]-2-[2-(2-furoylamino)ethylthio]acetamide

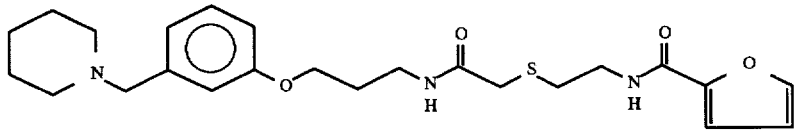

There was dissolved 1.12 g of 2-furancarboxylic acid in 50 ml of dichloromethane and added 2.06 g (0.01 mol) of DCC under cooling with ice and the mixture was stirred for 30 minutes. Thereto was added 3.65 g (0.01 mol) of N-[3-[3-(piperidinomethyl)phenoxy]propyl]-2-(2-aminoethylthio)acetamide and the mixture was stirred for 18 hours at room temperature. The precipitate was filtrated off, and the filtrate was washed with water and dried over Glauber's salt. Then the solvent was removed under reduced pressure and the residue was purified by silica gel column chromatography (chloroform:methanol=10:1) to give 1.2 g of the titled compound as crystals.

m.p.:60.5°–61.5° C.; MS(m/z):459(M$^+$); $^1$H-NMR (CDCl$_3$)δ: 1.43(2H, m), 1.57(4H, m), 2.02(2H, m), 2.37(4H, m), 3.27(2H, s), 3.43(2H, s), 3.50(2H, m), 3.61(2H, m), 4.05(2H, t), 6.47(1H, dd), 6.79(1H, dd), 6.84(1H, d), 6.93 (1H, s), 7.06(1H, br), 7.09(1H, d), 7.18(1H, t), 7.35(1H, br), 7.40(1h, s)

According to the same manner as in Example 1 hydrochloride thereof was prepared.

EXAMPLE 6

N-[3-[3-(piperidinomethyl)phenoxy]propyl-2-[2-(2-pyridinecarbonylamino)ethylthio]acetamide

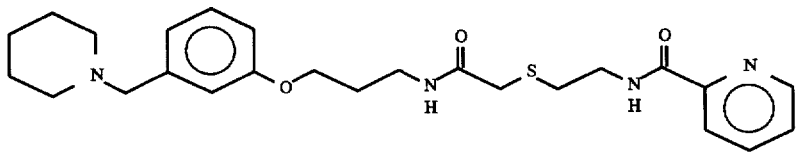

There was suspended 1.38 g (0.011 mol) of picolinic acid in 50 mg of dichloromethane and added 1.68 g (0.0 11 mol) of HOBt and 2.26 g (0.011 mol) of DCC under cooling with ice and the mixture was stirred for 30 minutes. Thereto was added 4.0 g (0.011 mol) of N-3-[3-(piperidinomethyl)phenoxy]propyl]-2-(2-aminoethylthio)acetamide and the mixture was stirred for 18 hours at room temperature. The precipitate was filtrated off, and the filtrate was washed with 10% 5 aqueous solution of sodium hydroxide and with water and dried over Glauber's salt. Then the solvent was removed under reduced pressure and the residue was purified by silica gel column chromatography (chloroform:methanol=20:1) to give 1.38 g of the titled compound as oily matter.

MS(m/z):470(M$^+$); $^1$HMR-CDCl$_3$)δ: 1.40(2H, m), 1.54 (4H, m), 2.01(2H, s), 2.35(4H, br), 2.32(2H, t), 3.29(2H, s), 3.41(2H, s), 3.49(2H, m), 3.67(2H, q) 4.02(2H, t), 6.77 (1H, dd), 6.89(2H, m), 7.17(1H, t), 7.38(1H, m), 7.55(1H, t), 7.79(1H, m), 8.13(1H, d), 8.46(1H, t), 8.51(1H, m)

According to the same manner as in Example 1 hydrochloride thereof was prepared.

EXAMPLE 7

N-[3-[3-(piperidinomethyl)phenoxy]propyl]-2-[2-[(N-cyanopropioimidoyl)amino]ethylthio]acetamide

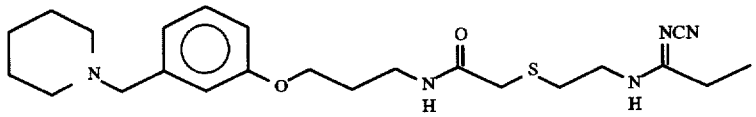

There were dissolved 4.0 g (0.0164 mol) of N-[3-[3-(piperidinomethyl)phenoxy]propyl]-2-(2-aminoethylthio) acetamide and 1.84 g (0.0164 mol) of methyl N-cyanopropioimidate in 40 ml of acetonitrile, and after reflux with heating for 3 hours, the solvent was removed under reduced pressure. The residue was purified by silica gel column chromatography (chloroform:ethanol=10:1) to give 2.65 g of the titled compound as oily matter.

MS(m/z):445(M$^+$); $^1$H-NMR(CDCl$_3$)δ: 1.28(3H, t), 1.50 (6H, m), 2.02(2H, m), 2.37(4H, m), 2.58(2H, q), 2.77(2H, t), 3.24(2H, s), 3.43 (2H, s), 3.48(4H, m), 4.04(2H, t), 6.77(1H, dd), 6.89(2H, m), 7.20(1H, t), 7.40(1H, t), 8.36(1H, t)

According to the same manner as in Example 1 hydrochloride thereof was prepared.

EXAMPLE 8

N-[4-[3-(piperidinomethyl) phenoxy]-cis-2-butenyl]-2-[2-(benzoylamino)ethylthio]acetamide

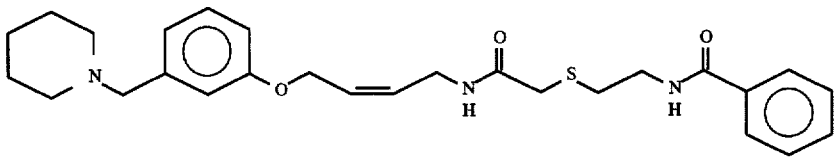

There was dissolved 0.97 g (0.008 mol) of benzoic acid in 60 ml of dichloromethane and added 1.22 g (0.00 mol) of HOBt and 1.65 g (0.0095 mol) of DCC under cooling with ice, and the mixture was stirred for 30 minutes under cooling with ice. Thereto was added 3.0 g (0.008 mol) of N-[4-[3-(piperidinomethyl) phenoxy]-cis-2-butenyl]-2-(2-aminoethylthio)acetamide and the mixture was stirred for 18 hours at room temperature. The precipitate was filtrated off, and the filtrate was washed with 5% aqueous solution of sodium hydroxide and with water and dried over Glauber's salt. Then the solvent was removed under reduced pressure and the residue was purified by silica gel column chromatography (chloroform:methanol=5:1) to give 0.9 g of the titled compound as oily matter.

MS(m/z):481(M$^+$) $^1$H-NMR(CDCl$_3$)δ: 1.44(2H, m), 1.63 (4H, m), 2.50(4H, br), 2.81 (2H, t), 3.25(2H, s), 3.57(2H, s), 3.65(2H, m), 3.95(2H, t), 4.61(2H, d), 5.66(1H, m), 5.80 (1H, m), 6.81(1H, dd) 6.88(1H, d), 6.99(1H, s), 7.20(1H, t), 7.40(3H, m), 7.81(2H, d).

According to the same manner as in Example 1 hydrochloride thereof was prepared.

EXAMPLE 9

N-[4-[3-(piperidinomethyl) phenoxy]-cis-2-butenyl]-2-[2-[(5-nitro)-2-furoylamino]ethylthio]acetamide

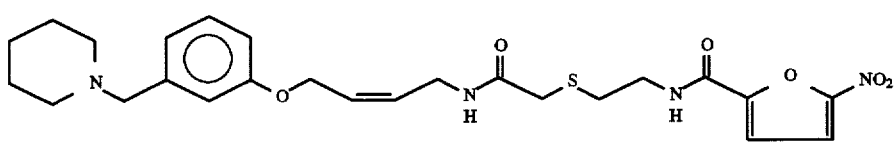

There was suspended 1.67 g (0.011 mol) of 5-nitro-2-furoic acid in 85 ml of dichloromethane and added 1.62 g (0.011 mol) of HOBt and 2.26 g (0.011 mol) of DCC under cooling with ice, and the mixture was stirred for 30 minutes. Thereto was added 4.0 g (0.011 mol) of N-[4-[3-(piperidinomethyl) phenoxy]-cis-2-butenyl]-2-(2-aminoethylthio)acetamide and the mixture was stirred for 18 hours at room temperature. The precipitate was filtrated off, and the filtrate was washed with 10% aqueous solution of sodium hydroxide and with water and dried over Glauber's salt. Then the solvent was removed under reduced pressure and the residue was purified by ilica gel column chromatography (chloroform:methanol=10:1) to give 0.60 g of the titled compound as oily matter.

MS(m/Z):516(M$^+$); $^1$H-NMR(CDCl$_3$)δ: 1.43(2H, m), 1.56(4H, m), 2.39(4H, br), 2.83 (2H, t), 3.27(2H, s), 3.45 (2H, s), 3.70(2H, q), 4.04(2H, t), 4.63(2H, d), 5.70(1H, m), 5.88(1H, m), 7.22(2H, m), 7.32(1H, d) 7.68(1H, br)

According to the same manner as in Example 1 hydrochloride thereof was prepared.

EXAMPLE 10

N-[4-[3-(piperidinomethyl) phenoxy]-cis-2-butenyl]-2-[2-(3-furoylamino)ethylthio]acetamide

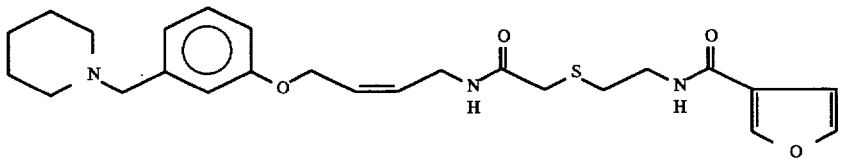

There was suspended 3.52 g (0.0154 mol) of 2-[(3-furoylamino)ethylthio]acetic acid in 80 ml of dichloromethane and added 2.36 g (0.0154 mol) of HOBt and 3.17 g (0.0154 mol) of DCC under cooling with ice, and the mixture was stirred for 30 minutes under cooling with ice. Thereto was added 4.0 g (0.0138 mol) of 4-[3-(piperidinomethyl)phenoxy]-cis-2-butenylamine, and the mixture was stirred for 12 hours at room temperature. The precipitate was filtrated off, and the filtrate was washed with 10% aqueous solution of sodium hydroxide and with water and dried over Glauber's salt. Then the solvent was removed under reduced pressure and the residue was purified by silica gel column chromatography (chloroform:methanol=10:1) to give 2.9 g of the titled compound as oily matter.

MS(m/z):471(M$^+$); $^1$H-NMR(CDCl$_3$)δ: 1.43(2H, m), 1.57 (4H, m), 2.38(4H, br), 2.77 (2H, t), 3.23(2H, s), 3.44(2H, s), 3.58(2H, q), 3.99(2H, t), 4.63(2H, d), 5.68(1H, m), 5.84(1H, m), 6.74(1H, d), 6.79(1H, dd), 6.90(2H, m), 7.20(1H, t), 7.33(1H, t), 7.39(1H, m), 7.54(1H, t), 8.01(1H, s)

According to the same manner as in Example 1 hydrochloride thereof was prepared.

EXAMPLE 11

N-[4-[3-(piperidinomethyl) phenoxy]-cis-2-butenyl]-2-[2-[(N-cyanopropioimidoyl)amino]ethylthio]-acetamide

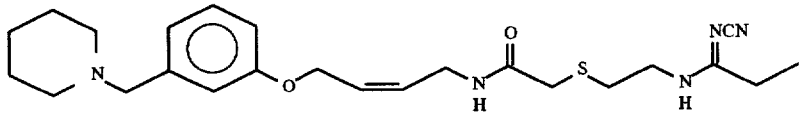

There were dissolved 4.0 g (0.0106 mol) of N-[4-[3-(piperidinomethyl) phenoxy]-cis-2-butenyl]-2-(2-aminoethylthio)acetamide and 2.01 g (0.0159 mol) of methyl N-cyanopropioimidate in 40 ml of acetonitrile, and after reflux with heating for 18 hours the solvent was removed under reduced pressure. The residue was purified by silica gel column chromatography (chloroform:ethanol= 10:1) to give 0.69 g of the titled compound as oily matter.

MS(m/z):457(M$^+$); $^1$H-NMR(CDCl$_3$)δ: 1.29(3H, t), 1.46 (6H, m), 1.60(4H, m), 2.47(4,H br), 2.61(2H, q), 2.78(2H, t), 3.24(2H, s), 3.51(4H, m), 3.99(2H, t), 4.65(2H, d), 5.68(1H, m), 5.85(1H, m), 6.81(1H, dd), 6.91(2H, m), 7 22(1H, t), 7.39(1H, t), 8.32(1H, m)

According to the same manner as in Example 1 hydrochloride thereof was prepared.

EXAMPLE 12

N-[3-[3-(piperidinomethyl)phenoxy]propyl]-2-[2-(methoxycarbonylamino)ethylthio]acetamide

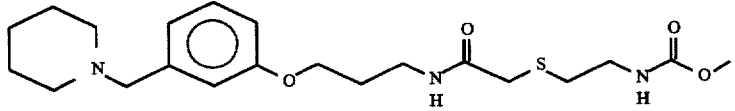

There was dissolved 2.07 g (0.011 mol) of 2-[2-(methoxycarbonylamino)ethylthio]acetic acid in 50 ml of dichloromethane and added 1.68 g (0.011 mol) of HOBt and 2.27 g (0.011 mol) of DCC under cooling with ice, and the mixture was stirred for 30 minutes under cooling with ice. Thereto was added 2.7 g (0.011 mol) of 3-[3-(piperidinomethyl)phenoxy]propylamine and the mixture was stirred for 18 hours at room temperature. The precipitate was filtrated off, and the filtrate was washed with 5% aqueous solution of sodium hydroxide and with water and dried over Glauber's salt. Then the solvent was removed under reduced pressure and the residue was purified by silica gel column chromatography (chloroform:methanol=5:1) to give 3.69 g of the titled compound as oily matter.

MS(m/z):423(M$^+$); $^1$HMR-CDCl$_3$)δ: 1.44(2H, m), 1.56 (4H, m) 2.03(2H, m), 2.38(4H, br), 2.69(2H, t), 3.23(2H, s), 3.37(2H, m), 3.45(2H, s), 3.51(2H, m), 3.64(3H, s), 4.07 (2H, t), 4.45(1H, br), 6.81(1H, dd), 6.90(1H, d), 6.96(1H, s), 7.21(1H, t), 7.27(1H, br)

According to the same manner as in Example 1 hydrochloride thereof was prepared.

EXAMPLE 13

N-[3-[3-(piperidinomethyl)phenoxy]propyl]-2-[2-(ethoxycarbonylamino)ethylthio]acetamide

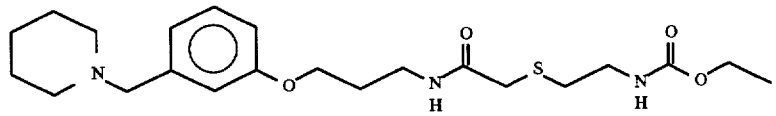

There was dissolved 2.5 g (0.012 mol) of 2-[2-(ethoxycarbonylamino)ethylthio]acetic acid in 60 ml of dichloromethane and added 1. 8 5 g (0. 0 12 mol) of HOBt and 2.5 g (0.012 mol) of DCC under cooling with ice, and the mixture was stirred for 30 minutes under cooling with ice. Thereto was added 3.0 g (0.012 mol) of 3-[3-(piperidinomethyl)phenoxy]propylamine and the mixture was stirred for 18 hours at room temperature. The precipitate was filtrated off, and the filtrate was washed with 5% aqueous solution of sodium hydroxide and with water and dried over Glauber's salt. Then the solvent was removed under reduced pressure and the residue was purified by silica gel column chromatography (chloroform: methanol =5 : 1) to give 4.23 g of the titled compound as oily matter.

MS(m/z):437(M$^+$); $^1$H-NMR(CDCl$_3$)δ: 1.20(3H, t) 1.43 (2H, m), 1.57(4H, m), 2.04(2H, m), 2.38(4H, br), 2.68(2H, t), 3.23(2H, s), 3.35(2H, m), 3.44(2H, s), 3.50(2H, q) 4.07(2H, t), 5.50(1H, br), 6.80(1H, dd), 6.89)1H, d), 6.95 (1H, s), 7.21(1H, t), 7.35(1h, br)

According to the same manner as in Example 1 hydrochloride thereof was prepared.

EXAMPLE 14

N-[4-[3-(piperidinomethyl) phenoxy]-cis-2-butenyl]-2-[2-(ethoxycarbonylamino)ethylthio]acetamide

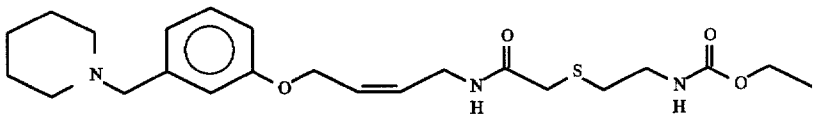

There was dissolved 2.7 g (0.0072 mol) of N-[4-[3-(piperidinomethyl) phenoxy]-cis-2-butenyl]-2-(2-aminoethylthio)acetamide in 20 ml of pyridine and added dropwise 0.78 g (0.0072 mol) of ethylchlorocarbonate under cooling with ice, and the mixture was stirred for 18 hours at room temperature. The obtained reaction mixture was poured into ice water and saturated with sodium chloride. The deposited oily matter was extracted with chloroform and washed with saturated aqueous solution of sodium chloride, and then dried over Glauber's salt. Then the solvent was removed under reduced pressure. The residue was purified by silica gel column chromatography (chloroform:methanol=10:1) to give 0.8 g of the titled compound as oily matter.

MS(m/z):449(H⁺); ¹H-NMR(CDCl₃)δ: 1.22(2H, t), 1.44 (2H, m), 1.60(4H, m), 2.39(4H, br), 2.68(2H, t), 3.22(2H, s), 3.36(2H, m), 3.45(2H, s), 4.01(2H, t), 4 09(2H, q), 4.64(2H, d), 5.35(1H, br), 5.70(1H, m), 5.87(1H, m), 6.80(1H, dd), 6.89(1H, d), 6.93(1H, s) , 7.08 (1H, br), 7.21(1H, t)

According to the same manner as in Example 1 hydrochloride thereof was prepared.

EXAMPLE 15

N-[4-[3-(piperidinomethyl) phenoxy]-cis-2-butenyl]-2-[2-(methoxycarbonylamino)ethylthio]acetamide

There was dissolved 1.84 g (0.0095 mol) of 2-(methoxycarbonylamino)ethylthioacetic acid in 50 ml of dichloromethane and added 1.45 g (0.0095 mol) of HOBt and 1.96 g (0.0095 mol) of DCC under cooling with ice, and the mixture was stirred for 30 minutes under cooling with ice. Thereto was added 2.48 g (0.0095 mol) of 4-[3-(piperidinomethyl)phenoxy]-cis-2-butenylamine and the mixture was stirred for 18 hours at room temperature. The precipitate was filtrated off, and the filtrate was washed with 5% aqueous solution of sodium hydroxide and with water and dried over Glauber's salt. Then the solvent was removed under reduced pressure and the residue was purified by silica gel column chromatography (chloroform:methanol=5:1) to give 2.3 g of the titled compound as oily matter.

MS(m/z):435(M⁺); ¹H-NMR(CDCl₃)δ: 1.44(2H, m), 1.58 (4H, m), 2.39(4H, br), 2.68 (2H, t), 3.22(2H, s), 3.37(2H, m), 3.45(2H, s), 3.66(3H, s), 4.02(2H, t), 4.64(2H, d), 5.38(1H, br), 5.70(1H, m), 5.88(1H, m), 6.80(1H, dd), 6.91(1H, d), 6.93(1H, s), 7.21(1H, t)

According to the same manner as in Example 1 hydrochloride thereof was prepared.

EXAMPLE 16

N-[3-[3-(piperidinomethyl) phenoxypropyl]-2-[2-[(N'-methylthioureido)ethylthio]acetamide

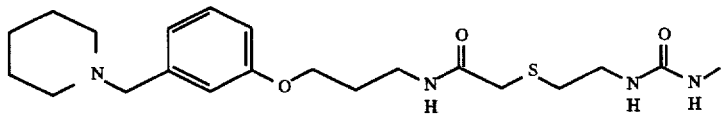

There was dissolved 3.0 g (0.0082 mol) of N-[3-[3-(piperidinomethyl)phenoxy]propyl]-2-(2-amino-ethylthio) acetamide in 50 ml of chloroform. Thereto was added dropwise a solution of 0.6 g (0.0082 mol) of methyl isothiocyanate in 10 mg of chloroform, and then the mixture was refluxed with heating for 2 hours. The solvent was removed under reduced pressure and the residue was purified by silica gel column chromatography (chloroform:methanol=10:1) to give 1.3 g of the titled compound as oily matter.

MS(m/z):348(M⁺); ¹H-NMR(CDCl₃)δ: 1.43(2H, br), 1.56(4H, br), 2.01(2H, m), 2.38 (4H, br), 2.77(2H, t), 2.96(3H, d), 3.26(2H, s), 3.43(2H, s), 3.45(2h, t), 3.73(2H, br), 4.03(2H, t), 6.79(1H, d), 6.88(1H, d), 6.92(1H, d), 6.92(1H, br), 7.12(1H, br), 7.20(1H, t), 7.47(1H,br)

According to the same manner as in Example 1 hydrochloride thereof was prepared.

EXAMPLE 17

N-[4-[3-(piperidinomethyl) phenoxy]-cis-2-butenyl]-2-[2-(N'-ethylureido)ethylthio]acetamide

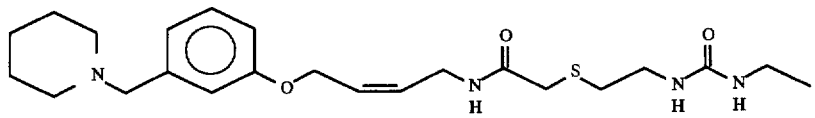

There was dissolved 2.94 g (0.014 mol) of 2-[2-(N'-ethylthioureido)-1-thio]acetic acid in 60 ml of dichloromethane and added 2.14 g (0. 0 14 mol) of HOBt and 2.94 g (0.014 mol) of DCC under cooling with ice, and the mixture was stirred for 30 minutes under cooling with ice. Thereto was added 3.75 g (0.014 mol) of 4-[3-(piperidinomethyl)phenoxy]-cis-2-butenylamine, and the mixture was stirred for 18 hours at room temperature. The precipitate was filtrated off, and the filtrate was washed with 5% aqueous solution of sodium hydroxide and with water and dried over Glauber's salt. Then the solvent was removed under reduced pressure and the residue was purified by silica gel column chromatography (chloroform:methanol=5:1) to give 2.2 g of the titled compound as crystals.

m.p.:90.2°–91.2° C.; MS(m/z):448(M$^+$); $^1$H-NMR (CDCl$_3$)δ: 1.09(3H, t), 1.45(2H, m), 1.58(4H, m), 2.42(4H, br), 2.67(2H, t), 3.17(2H, m), 3.23(2H, s), 3.37(2H, m), 3.48(2H, s), 4.65(2H, d), 4.82(1H, t), 5.34(1H, t), 5.71(1H, m), 5.83 (1H, m), 6.81(1H, dd), 6.90(1H, d), 6.96(1H, s), 7.22(1H, t), 7.28(1H, br)

According to the same manner as in Example 1 hydrochloride thereof was prepared.

In the following, various kinds of acetamide derivatives were prepared according to the same manner as above. The melting point, and the results of MS and NMR analysis, obtained as to the compounds of Examples, are shown in Tables 1 and 2.

TABLE 1

| Ex. | R$^1$\N\R$^2$ | R$^3$ | n | Y | R$^0$ | m.p. °C. | MS(M$^+$) | $^1$H—NMR(CDCl$_3$)δ: |
|---|---|---|---|---|---|---|---|---|
| 18 | piperidino (N—) | H | 0 | O | furan-2-yl | oily matter | 459 | 1.43(2H, m), 1.56(4H, m), 2.01(2H, m), 2.37(4H, m), 2.77(2H, t), 3.25(2H, s), 3.43(2H, s), 3.47(2H, m), 3.57(2H, m), 4.04(2H, t), 6.72(1H, s), 6.78(1H, dd), 6.88(1H, d), 6.92(1H, s), 7.20(1H, t), 7.39(1H, s), 7.42(2H, br), 7.98(1H, s) |
| 19 | piperidino (N—) | H | 0 | O | thiophen-2-yl | oily matter | 475 | 1.41(2H, m), 1.54(4H, m), 1.99(2H, m), 2.35(4H, m), 2.78(2H, t), 3.25(2H, s), 3.41(2H, s), 3.46(2H, m), 3.60(2H, q), 4.00(2H, t), 6.77(1H, dd), 6.88(2H, m), 7.01(1H, m), 7.17(1H, t), 7.41(1H, t), 7.55(1H, t), 7.69(1H, dd), 7.87(1H, t) |
| 20 | piperidino (N—) | H | 0 | O | pyridin-2-yl | oily matter | 470 | 1.42(2H, m), 1.56(4H, m), 1.97(2H, m), 2.37(4H, m), 2.49(2H, t), 2.78(2H, t), 2.86(2H, t), 3.45(4H, m), 3.68(2H, q), 4.02(2H, t), 6.67(1H, t), 6.75(1H, dd), 6.89(2H, m), 7.19(1H, t), 7.33(1H, m), 7.81(1H, t), 8.18(1H, dt), 8.67(1H, dd), 8.08(1H, d) |
| 21 | piperidino (N—) | H | 0 | O | —CH$_3$ | oily matter | 407 | 1.44(2H, m), 1.57(4H, m), 1.92(3H, s), 2.00(2H, m), 2.38(4H, m), 2.70(2H, t), 3.23(2H, s), 3.43(2H, s), 3.45(2H, m), 3.46(2H, m), 4.07(2H, t), 6.56(1H, br), 6.79(1H, dd), 6.90(1H, d), 6.94(1H, s), 7.21(1H, t), 7.34(1H, br) |
| 22 | pyrrolidino (N—) | H | 0 | O | furan-2-yl | oily matter | 445 | 1.78(4H, m), 2.02(2H, t), 2.52(4H, m), 2.78(2H, t), 3.27(2H, s), 3.49(2H, m), 3.59(2H, s), 3.62(2H, m), 4.05(2H, t), 6.47(1H, dd), 6.79(1H, dd), 6.91(1H, d), 6.95(1H, s), 7.04(1H, br), 7.10(1H, d), 7.20(1H, t), 7.32(1H, br), 7.40(1H, s) |

TABLE 1-continued

[Structure: R¹R²N-CH₂-phenyl(R³)-O-CH₂CH₂CH₂-NH-C(O)-CH₂-S(O)ₙ-CH₂CH₂-NH-C(Y)-R⁰]

| Ex. | R¹R²N- | R³ | n | Y | R⁰ | m.p. °C. | MS(M⁺) | ¹H—NMR(CDCl₃)δ: |
|---|---|---|---|---|---|---|---|---|
| 23 | (CH₃)(CH₃)N— | H | 0 | O | furan-2-yl | 56.5–57.5 | 419 | 2.01(2H, t), 2.23(6H, s), 2.78(2H, t), 3.26(2H, s), 3.38(2H, s), 3.50(2H, m), 3.60(2H, m), 4.04(2H, t), 6.46(1H, d), 6.81(1H, d), 6.82(1H, d), 6.89(1H, s), 7.09(1H, d), 7.21(1H, t), 7.32(1H, br), 7.42(1H, s), 7.50(1H, br) |
| 24 | (CH₃CH₂CH₂)(CH₃CH₂CH₂)N— | H | 0 | O | furan-2-yl | oily matter | 475 | 0.86(6H, t), 1.47(4H, m), 2.05(2H, t), 2.37(4H, t), 2.79(2H, t), 3.27(2H, s), 3.52(4H, m), 4.06(2H, t), 3.63(2H, m), 6.47(1H, dd), 6.78(1H, dd), 6.86(1H, br), 6.92(1H, d), 6.97(1H, s), 7.09(1H, d), 7.17(1H, t) 7.23(1H, br), 7.40(1H, s) |
| 25 | piperidin-1-yl | H | 0 | O | pyrrol-2-yl (NH) | oily matter | 458 | 1.41(2H, m), 1.54(4H, m), 1.97(2H, m), 2.38(4H, m), 2.74(2H, t), 3.23(2H, s), 3.43(4H, m), 3.56(2H, q), 3.96(2H, t), 6.15(1H, t), 6.76(2H, m), 6.86(3H, m), 7.17(1H, t), 7.63(2H, m), 10.67(1H, s) |
| 26 | piperidin-1-yl | H | 0 | O | —OCH₂CH₂CH₃ | oily matter | 451 | 0.91(3H, t), 1.44(2H, m), 1.57(4H, m), 2.03(2H, m), 2.38(4H, br), 2.69(2H, t), 3.23(2H, s), 3.36(2H, m), 3.44(2H, s), 3.51(2H, m), 3.98(2H, t), 4.07(2H, t), 5.38(1H, br), 6.80(1H, dd), 6.90(1H, d), 6.95(1H, s), 7.21(1H, t), 7.27(1H, br) |
| 27 | piperidin-1-yl | H | 0 | O | —OCH₂CH₂CH₂CH₃ | oily matter | 465 | 0.91(3H, t), 1.35(2H, m), 1.44(2H, m), 1.57(6H, m), 2.03(2H, m), 2.39(4H, br), 2.69(2H, t), 3.23(2H, s), 3.36(2H, m), 3.45(2H, s), 3.51(2H, m), 4.07(4H, m), 5.37(1H, br), 6.80(1H, dd), 6.90(1H, d), 6.97(1H, s), 7.21(1H, t), 7.29(1H, br) |
| 28 | piperidin-1-yl | H | 0 | O | —OCH₂CH(CH₃)CH₃ | oily matter | 465 | 0.90(6H, d), 1.44(2H, m), 1.58(4H, m), 1.89(1H, m), 2.03(2H, m), 2.38(4H, br), 2.69(2H, t), 3.23(2H, s), 3.36(2H, m), 3.45(2H, s), 3.51(2H, m), 3.81(2H, d), 4.07(2H, t), 5.35(1H, br), 6.80(1H, dd), 6.90(1H, d), 6.96(1H, s), 7.21(1H, t), 7.27(1H, br) |
| 29 | piperidin-1-yl | H | 0 | O | —OCH₂CH₂OCH₃ | oily matter | 467 | 1.46(2H, m), 1.59(4H, m), 2.03(2H, m), 2.39(4H, br), 2.69(2H, t), 3.23(2H, s), 3.37(3H, s), 3.38(2H, m), 3.45(2H, s), 3.54(4H, m), 4.07(2H, t), 4.19(2H, t), 5.42(1H, br), 6.80(1H, dd), 6.90(1H, d), 6.95(1H, s), 7.21(1H, t), 7.24(1H, br) |
| 30 | piperidin-1-yl | H | 0 | O | —NHCH₃ | oily matter | 422 | 1.43(2H, m), 1.56(4H, m), 2.04(2H, t), 2.37(4H, br), 2.68(2H, m), 2.69(3H, d), 3.23(2H, s), 3.35(2H, m), 3.42(2H, s), 3.44(2H, m), 4.04(2H, t), 6.78(1H, d), 6.90(2H, m), 7.20(1H, t), 7.56(1H, br) |
| 31 | piperidin-1-yl | H | 0 | O | —NHCH₂CH₃ | 92.3–94.5 | 436 | 1.05(3H, t), 1.51(6H, m), 2.03(2H, m), 2.36(4H, m), 2.67(2H, t), 3.14(2H, m), 3.24(2H, s), 3.43(2H, s), 3.48(4H, m), 4.06(2H, t), 4.76(1H, t), 5.40(1H, t), 6.80(1H, dd), 6.89(1H, d), 6.96(1H, s), 7.21(1H, t), 7.45(1H, t) |

TABLE 1-continued

[Structure: R¹R²N-CH₂-(phenyl with R³)-O-(CH₂)₃-NH-C(=O)-CH₂-S(=(O)ₙ)-CH₂CH₂-NH-C(=Y)-R⁰]

| Ex. | R¹\\N/R² | R³ | n | Y | R⁰ | m.p. °C | MS(M⁺) | ¹H—NMR(CDCl₃)δ: |
|---|---|---|---|---|---|---|---|---|
| 32 | piperidin-N— | H | 0 | S | —NHCH₂CH₃ | oily matter | 452 | 1.17(3H, t), 1.44(2H, br), 1.56(4H, br), 2.03(2H, m), 2.78(2H, t), 3.25(2H, s), 3.45(2H, s), 3.47(4H, m), 3.75(2H, m), 4.05(2H, t), 6.48(1H, br), 6.80(1H, dd), 6.89(1H, d), 6.94(1H, s), 7.21(1H, t), 7.27(1H, br) |
| 33 | piperidin-N— | H | 0 | S | —NHCH₂CH₂—CH₂CH₃ | oily matter | 480 | 0.91(3H, t), 1.44(6H, m), 1.56(4H, m), 2.04(2H, m), 2.23(2H, m), 2.39(4H, br), 2.80(2H, t), 3.25(2H, s), 3.44(2H, s), 3.49(2H, m), 3.76(2H, m), 4.06(3H, t), 6.30(1H, br), 6.80(1H, dd), 6.87(1H, br), 6.89(1H, d), 6.94(1H, s), 7.15(1H, br), 7.22(1H, t) |
| 34 | piperidin-N— | H | 0 | S | —NHCH₂CH=CH₂ | oily matter | 464 | 1.45(2H, br), 1.57(4H, br), 2.03(2H, m), 2.40(4H, br), 2.78(2H, t), 3.25(2H, s), 3.44(2H, s), 3.49(2H, m), 3.77(2H, m), 4.06(4H, m), 5.19(2H, m), 5.84(1H, m), 6.52(1H, br), 6.80(1H, dd), 6.89(1H, d), 6.95(1H, s), 7.16(1H, br), 7.22(1H, t) |
| 35 | piperidin-N— | H | 0 | S | —NH-phenyl | oily matter | 500 | 1.42(2H, m), 1.56(4H, m), 2.00(2H, m), 2.40(4H, m), 2.81(2H, t), 3.22(2H, s), 3.45(2H, s), 3.45(2H, m), 3.83(2H, m), 4.04(2H, t), 6.75(1H, t), 6.80(1H, dd), 6.88(1H, d), 6.97(1H, s), 7.25(5H, m), 7.40(1H, t), 8.35(1H, br) |
| 36 | piperidin-N— | H | 0 | =N—CN | —H | oily matter | 417 | 1.51(6H, m), 2.02(2H, m), 2.42(4H, m), 2.78(2H, t), 3.26(2H, s), 3.45(2H, s), 3.49(4H, m), 4.05(2H, t), 6.80(1H, dd), 6.88(1H, d), 6.95(1H, s), 7.21(1H, t), 7.50(1H, t), 7.89(1H, s), 8.80(1H, br) |
| 37 | piperidin-N— | H | 0 | =N—CN | —CH₃ | oily matter | 431 | (DMSO-d₆) 1.47(2H, m), 1.61(4H, m), 2.01(2H, m), 2.28(3H, s), 2.51(4H, m), 2.77(2H, t), 3.23(2H, s), 3.45(4H, m), 3.57(2H, s), 4.04(2H, t), 6.81(1H, dd), 6.92(2H, m), 7.21(1H, t), 7.81(1H, t), 8.79(1H, t) |
| 38 | piperidin-N— | H | 0 | =N—CN | —CH(CH₃)₂ | oily matter | 459 | 1.44(2H, m), 1.55(4H, m), 2.02(2H, m), 2.21(1H, m), 2.41(6H, m), 2.46(2H, t), 3.24(2H, s), 3.43(2H, s), 3.50(4H, m), 4.05(2H, t), 6.79(1H, dd), 6.87(2H, m), 7.20(1H, t), 7.48(1H, t), 8.34(1H, br) |
| 39 | piperidin-N— | H | 0 | =N—CN | —CH₂CH₂CH₃ | oily matter | 459 | 0.99(3H, t), 1.50(6H, m), 1.75(2H, m), 2.01(2H, m), 2.37(4H, m), 2.54(2H, t), 2.77(2H, t), 3.24(2H, s), 3.42(2H, s), 3.46(4H, m), 4.03(2H, t), 6.78(2H, dd), 6.89(2H, m), 7.19(1H, t), 7.55(1H, t), 8.51(1H, m) |
| 40 | piperidin-N— | H | 0 | =N—CN | —phenyl | oily matter | 493 | 1.47(2H, m), 1.62(4H, m), 1.93(2H, t), 2.61(4H, m), 2.82(2H, t), 3.19(2H, s), 3.55(2H, q), 3.59(2H, m), 3.69(2H, s), 3.99(2H, t), 6.86(2H, m), 6.98(1H, s), 7.21(1H, t), 7.43(4H, m), 7.85(1H, m), 8.49(1H, br) |

TABLE 1-continued

| Ex. | R¹,R² N | R³ | n | Y | R⁰ | m.p. °C. | MS(M⁺) | ¹H—NMR(CDCl₃)δ: |
|---|---|---|---|---|---|---|---|---|
| 41 | piperidin-N— | H | 0 | =N—CN | —CH₂-phenyl | oily matter | 507 | 1.42(2H, m), 1.54(4H, m), 1.96(2H, m), 2.38(4H, m), 2.71(2H, t), 3.13(2H, s), 3.44(4H, m), 3.43(2H, s), 3.87(2H, s), 4.00(2H, t), 6.77(1H, dd), 6.90(2H, m), 7.17(1H, t), 7.29(6H, m), 8.26(1H, t) |
| 42 | piperidin-N— | H | 0 | =N—CN | thiophene | oily matter | 499 | 1.44(2H, m), 1.57(4H, m), 1.98(2H, m), 2.45(4H, m), 2.84(2H, t), 3.24(2H, s), 3.43(2H, q), 3.50(2H, s), 3.66(2H, t), 4.01(2H, t), 6.79(1H, dd), 6.89(2H, m), 7.09(1H, m), 7.19(1H, t), 7.39(1H, m), 7.51(1H, d), 7.89(1H, d) |
| 43 | piperidin-N— | H | 0 | =N—CN | pyridine | oily matter | 494 | 1.42(2H, m), 1.55(4H, m), 2.01(2H, m), 2.38(4H, m), 2.80(2H, t), 3.28(2H, s), 3.42(2H, s), 3.48(2H, s), 3.66(2H, m), 4.04(2H, t), 6.84(3H, m), 7.19(1H, m), 7.41(1H, t), 7.55(1H, t), 7.81(1H, t), 8.10(1H, d), 8.46(1H, d), 8.53(1H, d) |
| 44 | piperidin-N— | H | 0 | O | 2-F-phenyl | oily matter | 487 | 1.42(2H, m), 1.56(4H, m), 2.02(2H, m), 2.36(4H, bs), 2.82(2H, b), 3.28(2H, s), 3.43(2H, s), 3.51(2H, s), 3.68(2H, m), 4.05(2H, t), 6.80(1H, dd), 6.90(1H, d), 6.92(1H, s), 7.20(6H, m), 7.45(1H, m), 8.04(1H, t) |
| 45 | piperidin-N— | H | 0 | O | 2-CF₃-phenyl | oily matter | 537 | 1.43(2H, m), 1.57(4H, m), 2.00(2H, m), 2.38(4H, bs), 2.80(2H, t), 3.24(2H, s), 3.43(2H, s), 3.47(2H, m), 3.63(2H, m), 4.03(2H, t), 6.66(1H, br), 6.77(1H, dd), 6.88(1H, d), 6.92(1H, s), 7.19(1H, t), 7.22(1H, br), 7.51(3H, m), 7.67(1H, d) |
| 46 | piperidin-N— | H | 0 | O | 2-OCH₃-phenyl | oily matter | 499 | 1.42(2H, m), 1.57(4H, m), 2.02(2H, m), 2.38(4H, bs), 2.80(2H, t), 3.29(2H, s), 3.44(2H, s), 3.50(2H, s), 3.66(2H, m), 3.96(3H, s), 4.03(2H, t), 6.78(1H, dd), 6.89(1H, d), 6.91(1H, s), 6.97(1H, d), 7.06(1H, d), 7.19(1H, t), 7.43(1H, d), 7.44(1H, br), 8.17(1H, d), 8.26(1H, br) |
| 47 | piperidin-N— | H | 0 | O | 2-NO₂-phenyl | oily matter | 514 | 1.44(2H, m), 1.58(4H, m), 2.00(2H, m), 2.39(4H, bs), 2.88(2H, t), 3.27(2H, s), 3.42(2H, s), 3.47(2H, m), 3.67(2H, m), 4.03(2H, t), 6.77(1H, dd), 6.90(1H, d), 7.16(1H, s), 7.14(1H, br), 7.18(1H, t), 7.52(2H, m), 7.60(1H, m), 7.98(1H, d) |
| 48 | piperidin-N— | H | 1 | O | —OCH₃ | 84.3–86.5 | 467 | 1.44(2H, m), 1.59(4H, m), 2.02(2H, m), 2.40(4H, bs), 3.04(2H, m), 3.42(1H, d), 3.46(2H, s), 3.52(2H, m), 3.64(2H, m), 3.66(3H, s), 3.69(1H, d), 4.04(2H, t), 5.67(1H, br), 6.78(1H, dd), 6.89(1H, d), 6.94(1H, s), 7.16(1H, br), 7.20(1H, t) |

TABLE 2

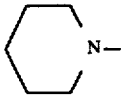

| Ex. | R¹R²N | R³ | n | Y | R⁰ | m.p. °C. | MS(M⁺) | ¹H—NMR(CDCl₃)δ: |
|---|---|---|---|---|---|---|---|---|
| 49 | piperidino | H | 0 | O | 2-furyl | oily matter | 471 | 1.42(2H, m), 1.56(4H, m), 2.37(4H, br), 2.78(2H, t), 3.26(2H, s), 3.43(2H, s), 3.62(2H, q), 4.00(2H, t), 4.03(2H, d), 5.67(1H, m), 5.84(1H, m), 6.46(1H, m), 6.78(1H, dd), 6.89(2H, m), 7.10(1H, dd), 7.22(3H, m), 7.43(1H, dd) |
| 50 | piperidino | H | 0 | O | 2-pyridyl | oily matter | 482 | 1.43(2H, m), 1.56(4H, m), 2.36(4H, br), 2.82(2H, t), 3.29(2H, s), 3.43(2H, s), 3.70(4H, q), 4.02(2H, t), 4.63(2H, d), 5.68(1H, m), 5.84(1H, m), 6.78(1H, dd), 6.90(2H, m), 7.27(2H, m), 7.41(1H, m), 7.81(1H, m), 8.16(1H, d), 8.41(1H, t), 8.54(1H, d) |
| 51 | piperidino | H | 0 | O | —CH₂-(2-thienyl) | oily matter | 501 | 1.43(2H, m), 1.55(4H, m), 2.37(4H, br), 2.65(2H, t), 3.17(2H, s), 3.41(4H, m), 3.73(2H, s), 3.96(2H, t), 4.62(2H, d), 5.69(1H, m), 5.87(1H, m), 6.78(1H, dd), 6.90(5H, m), 7.22(3H, m) |
| 52 | piperidino | H | 0 | O | 2-thienyl | oily matter | 487 | 1.43(2H, m), 1.56(4H, m), 2.37(4H, br), 2.78(2H, t), 3.25(2H, s), 3.43(2H, s), 3.63(2H, m), 4.01(2H, t), 4.62(2H, d), 5.67(1H, m), 5.84(1H, m), 6.77(1H, dd), 6.89(1H, d), 6.91(1H, s), 7.02(1H, br), 7.04(1H, t), 7.20(1H, t), 7.21(1H, br), 7.44(1H, d), 7.59(1H, d) |
| 53 | piperidino | H | 0 | O | 3-thienyl | oily matter | 487 | 1.43(2H, m), 1.57(4H, m), 2.38(4H, br), 2.79(2H, t), 3.24(2H, s), 3.44(2H, s), 3.61(2H, m), 4.00(2H, t), 4.62(2H, d), 5.67(1H, m), 5.84(1H, m), 6.78(1H, d), 6.89(1H, d), 6.91(1H, s), 7.13(1H, br), 7.20(1H, t), 7.29(1H, m), 7.35(1H, br), 7.45(1H, d), 7.95(1H, d) |
| 54 | piperidino | H | 0 | O | —CH₂OCH₃ | oily matter | 449 | 1.43(2H, m), 1.57(4H, m), 2.37(4H, br), 2.71(2H, t), 3.23(2H, s), 3.40(3H, s), 3.44(2H, s), 3.50(2H, m), 3.88(2H, s), 4.01(2H, m), 4.64(2H, d), 5.68(1H, m), 5.86(1H, m), 6.80(1H, dd), 6.90(1H, d), 6.92(1H, s), 7.20(1H, t), 7.22(1H, br) |
| 55 | piperidino | H | 0 | O | —CH₂OCOCH₃ | oily matter | 477 | 1.44(2H, m), 1.57(4H, m), 2.16(3H, s), 2.38(4H, br), 2.72(2H, t), 3.22(2H, s), 3.44(2H, s), 3.51(2H, q), 4.00(2H, t), 4.55(2H, s), 4.63(2H, d), 5.68(1H, m), 5.86(1H, m), 6.79(1H, dd), 6.90(2H, m), 7.17(3H, m) |
| 56 | piperidino | H | 0 | O | 3-fluorophenyl | oily matter | 499 | 1.43(2H, m), 1.56(4H, m), 2.38(4H, br), 2.82(2H, t), 3.24(2H, s), 3.44(2H, s), 3.65(2H, m), 4.01(2H, t), 4.62(2H, d), 5.67(1H, m), 5.86(1H, m), 6.78(1H, dd), 6.89(1H, d), 6.91(1H, s), 6.94(1H, br), 7.18(2H, m), 7.34(1H, br), 7.36(1H, m), 7.58(2H, m) |
| 57 | piperidino | H | 0 | O | 3-(trifluoromethyl)phenyl | oily matter | 549 | 1.43(2H, m), 1.56(4H, m), 2.37(4H, br), 2.84(2H, t), 3.24(2H, s), 3.44(2H, s), 3.67(2H, m), 4.01(2H, t), 4.61(2H, d), 5.66(1H, m), 5.86(1H, m), 6.78(1H, dd), 6.89(1H, d), 6.90(1H, br), 6.91(1H, s), 7.20(1H, t), 7.53(1H, t), 7.67(1H, br), 7.73(1H, d), 8.03(1H, d), 8.14(1H, s) |

TABLE 2-continued

| Ex. | R¹R²N- | R³ | n | Y | R⁰ | m.p. °C. | MS(M⁺) | ¹H—NMR(CDCl₃)δ: |
|---|---|---|---|---|---|---|---|---|
| 58 | piperidino | H | 0 | O | 3,4-dimethoxyphenyl | oily matter | 541 | 1.43(2H, m), 1.59(4H, m), 2.42(4H, br), 2.81(2H, t), 3.25(2H, s), 3.49(2H, s), 3.65(2H, m), 3.90(3H, s), 3.91(3H, s), 3.99(2H, t), 4.62(2H, d), 5.66(1H, m), 5.84(1H, m), 6.78(1H, dd), 6.84(1H, d), 6.89(1H, d), 6.94(1H, s), 7.05(1H, br), 7.17(1H, br), 7.20(1H, t), 7.37(1H, dd), 7.46(1H, d) |
| 59 | piperidino | H | 0 | O | 2-furyl | oily matter | 485 | 1.43(2H, m), 1.58(4H, m), 2.32(3H, s), 2.38(4H, br), 2.78(2H, t), 3.26(2H, s), 3.45(2H, s), 3.61(2H, q), 4.01(2H, t), 4.64(2H, d), 5.69(1H, m), 5.85(1H, m), 6.08(1H, dd), 6.79(1H, dd), 6.91(2H, m), 7.00(1H, d), 7.23(2H, m) |
| 60 | piperidino | H | 0 | O | 3-methyl-2-methyl-furyl | oily matter | 485 | 1.47(2H, m), 1.65(4H, m), 2.54(4H, br), 1.58(3H, d), 2.78(2H, t), 3.24(2H, s), 3.58(4H, m), 3.97(2H, t), 4.62(2H, d), 5.67(1H, m), 5.81(1H, m), 6.56(1H, d), 6.82(1H, dd), 6.90(1H, d), 6.98(1H, s), 7.22(3H, m) |
| 61 | piperidino | 2-OCH₃ | 0 | O | 2-furyl | oily matter | 501 | 1.43(2H, m), 1.57(4H, m), 2.36(4H, br), 2.80(2H, t), 3.24(2H, s), 3.40(2H, s), 3.63(2H, m), 3.86(3H, s), 4.00(2H, t), 4.68(2H, d), 5.75(1H, m), 5.90(1H, m), 6.48(1H, dd), 6.83(2H, m), 6.91(1H, s), 7.04(1H, br), 7.11(1H, d), 7.12(1H, br), 7.42(1H, s) |
| 62 | piperidino | 2-OCH₃ | 1 | O | 2-furyl | 112.0–113.0 | 517 | 1.44(2H, m), 1.60(4H, m), 2.42(4H, br), 3.14(1H, m), 3.23(1H, m), 3.47(2H, s), 3.54(1H, d), 3.75(1H, d), 3.85(3H, s), 3.86(2H, m), 4.00(2H, t), 4.71(2H, d), 5.73(1H, m), 5.88(1H, m), 6.70(1H, d), 6.82(2H, s), 6.98(1H, s), 7.39(1H, d), 7.40(2H, br), 7.99(1H, s) |
| 63 | piperidino | 2-NO₂ | 0 | O | 2-furyl | oily matter | 516 | 1.45(2H, m), 1.58(4H, m), 2.37(4H, m), 2.80(2H, t), 3.27(2H, s), 3.48(2H, s), 3.63(2H, m), 4.02(2H, t), 4.80(2H, d), 5.85(2H, m), 6.48(1H, dd), 7.00(1H, d), 7.05(1H, br), 7.10(1H, d), 7.16(1H, s), 7.18(1H, br), 7.44(1H, s), 7.80(1H, d) |
| 64 | piperidino | 2-NO₂ | 0 | O | 2-furyl | oily matter | 516 | 1.45(2H, m), 1.59(4H, m), 2.38(4H, br), 2.80(2H, t), 3.26(2H, s), 3.48(2H, s), 3.61(2H, m), 4.03(2H, t), 4.80(2H, d), 5.86(2H, m), 6.72(1H, d), 7.00(1H, d), 7.03(1H, br), 7.11(1H, br), 7.16(1H, s), 7.41(1H, d), 7.81(1H, d), 8.00(1H, s) |
| 65 | piperidino | H | 0 | O | —OCH₂CH₂CH₃ | oily matter | 463 | 0.92(3H, t), 1.44(2H, m), 1.57(6H, m), 2.38(4H, br), 2.68(2H, t), 3.22(2H, s), 3.37(2H, m), 3.44(2H, s), 4.01(4H, m), 4.64(2H, d), 5.20(1H, br), 5.71(1H, m), 5.88(1H, m), 6.79(1H, dd), 6.90(1H, d), 6.92(1H, s), 6.93(1H, br), 7.21(1H, t) |
| 66 | piperidino | H | 0 | O | —OCH₂CH₂CH₂CH₃ | oily matter | 477 | 0.92(3H, t), 1.40(4H, m), 1.56(6H, m), 2.38(4H, br), 2.68(2H, t), 3.22(2H, s), 3.36(2H, m), 3.44(2H, s), 4.03(4H, m), 4.64(2H, d), 5.70(1H, m), 5.87(1H, m), 6.81(1H, dd), 6.89(1H, d), 6.92(1H, s), 6.95(1H, br), 7.21(1H, t) |

TABLE 2-continued

| Ex. | R¹R²N- | R³ | n | Y | R⁰ | m.p. °C | MS(M⁺) | ¹H-NMR(CDCl₃)δ: |
|---|---|---|---|---|---|---|---|---|
| 67 | piperidin-1-yl | H | 0 | O | -OCH₂CH(CH₃)CH₃ | oily matter | 477 | 0.91(6H, d), 1.43(2H, m), 1.57(4H, m), 1.89(1H, m), 2.36(4H, br), 2.68(2H, t), 3.22(2H, s), 3.37(2H, m), 3.44(2H, s), 3.83(2H, d), 4.02(2H, t), 4.64(2H, d), 5.24(1H, br), 5.71(1H, m), 5.87(1H, m), 6.79(1H, dd), 6.90(1H, d), 6.91(1H, s), 6.96(1H, br), 7.21(1H, t) |
| 68 | piperidin-1-yl | H | 0 | O | -OCH₂CH₂OCH₃ | oily matter | 479 | 1.45(2H, m), 1.57(4H, m), 2.37(4H, br), 2.68(2H, t), 3.22(2H, s), 3.37(3H, s), 3.38(2H, m), 3.55(2H, m), 4.02(2H, t), 4.22(2H, t), 4.64(2H, d), 5.36(1H, br), 5.69(1H, m), 5.87(1H, m), 6.78(1H, dd), 6.90(1H, d), 6.92(1H, s), 6.97(1H, br), 7.21(1H, t) |
| 69 | piperidin-1-yl | H | 0 | O | -OCH₂CH=CH₂ | oily matter | 461 | 1.43(2H, m), 1.58(4H, m), 2.38(4H, br), 2.69(2H, t), 3.22(2H, s), 3.38(2H, m) 3.45(2H, s), 4.02(2H, t), 4.55(2H, d), 4.64(2H, d), 5.26(2H, m), 5.40(1H, br), 5.70(1H, m), 5.88(2H, m), 6.80(1H, dd), 6.90(1H, d), 6.93(1H, s), 7.01(1H, br), 7.21(1H, t) |
| 70 | piperidin-1-yl | H | 0 | S | -NHCH₂CH₃ | oily matter | 464 | 1.19(3H, t), 1.43(2H, m), 1.66(4H, m), 2.39(4H, t), 1.78(2H, t), 3.26(2H, s), 3.45(4H, m), 3.70(2H, q), 3.98(2H, t), 4.63(2H, d), 5.67(1H, m), 5.85(1H, m), 6.79(2H, m), 6.90(2H, m), 7.20(2H, m), 7.40(1H, t) |
| 71 | piperidin-1-yl | H | 0 | O | furan-2-yl | oily matter | 496 | 1.44(2H, m), 1.58(4H, m), 2.42(4H, m), 2.83(2H, t), 3.26(2H s), 3.49(2H, s), 3.61(2H, q), 4.12(2H, q), 4.65(2H, d), 6.74(2H, m), 6.79(1H, dd), 6.92(2H, m), 7.19(2H, m) |
| 72 | piperidin-1-yl | H | 0 | O | 2-fluorophenyl | oily matter | 499 | 1.42(2H, m), 1.55(4H, m), 2.36(4H, m), 2.81(2H, m), 3.25(2H, s), 3.42(2H, s), 3.67(2H, d), 3.99(2H, t), 4.61(2H, d), 5.65(1H, m), 5.82(1H, m), 6.78(1H, dd), 6.89(2H, m), 7.09(1H, m), 7.20(2H, m), 7.35(2H, m), 7.45(1H, m), 8.00(1H, m) |
| 73 | piperidin-1-yl | H | 0 | O | 2-methoxyphenyl | oily matter | 511 | 1.43(2H, m), 1.57(4H, m), 2.36(4H, m), 2.80(2H, t), 3.28(2H, s), 3.44(2H, s), 3.66(2H, q), 3.97(3H, s), 4.00(2H, t), 4.61(2H, d), 5.66(1H, m), 5.81(1H, m), 6.77(1H, dd), 6.90(2H, m), 6.97(1H, d), 7.05(1H, m), 7.21(2H, m), 7.44(1H, m), 8.17(1H, dd), 8.25(1H, m) |
| 74 | piperidin-1-yl | H | 0 | O | 2-nitrophenyl | oily matter | 526 | 1.42(2H, m), 1.55(4H, m), 2.36(4H, m), 2.80(2H, t), 3.21(2H, s), 3.42(2H, s), 3.59(2H, q), 3.90(2H, t), 4.58(2H, m), 5.60(1H, m), 5.79(1H, m), 6.76(1H, dd), 6.88(2H, m), 7.16(2H, m), 7.50(3H, m), 7.62(1H, m), 7.95(1H, dd) |
| 75 | piperidin-1-yl | H | 1 | O | -OCH₂CH₃ | 64.7–66.1 | 465 | 1.24(3H, t), 1.43(2H, m), 1.57(4H, m), 2.38(4H, br), 3.05(2H, m), 3.41(1H, d), 3.44(2H, s), 3.65(2H, m), 3.70(1H, d), 4.03(2H, t), 4.11(2H, q), 4.63(2H, d), 5.53(1H, br), 5.65(1H, m), 5.68(1H, m), 6.79(1H, dd), 6.90(2H, m), 7.10(1H, br), 7.21(1H, t) |

TABLE 2-continued

![structure: aromatic ring with R3 substituent, R1R2N-CH2- group, -O-CH2-CH=CH-CH2-NH-C(O)-CH2-S(O)n-CH2CH2-NH-C(Y)-R0]

| Ex. | R¹R²N | R³ | n | Y | R⁰ | m.p. °C. | MS(M⁺) | ¹H—NMR(CDCl₃)δ: |
|---|---|---|---|---|---|---|---|---|
| 76 | piperidin-1-yl | H | 1 | O | —OCH₂CH₂CH₂CH₃ | oily matter | 493 | 0.92(3H, t), 1.42(4H, m), 1.56(6H, m), 2.37(4H, br), 3.05(2H, m), 3.43(1H, d), 3.44(2H, s), 3.62(2H, m), 3.70(1H, d), 4.03(4H, m), 4.62(2H, d), 5.66(2H, m), 5.87(1H, m), 6.78(1H, dd), 6.90(2H, m), 7.21(1H, t), 7.24(1H, br) |
| 77 | piperidin-1-yl | 2-OCH₃ | 0 | O | —OCH₂CH₃ | oily matter | 479 | 1.24(3H, t), 1.44(2H, m), 1.58(4H, m), 2.37(4H, bs), 2.69(2H, t), 3.21(2H, s), 3.37(2H, m), 3.41(2H, s), 3.86(3H, s), 4.01(2H, t), 4.10(2H, q), 4.70(2H, d), 5.34(1H, br), 5.76(1H, m), 5.92(1H, m), 6.83(2H, m), 6.94(1H, s), 7.10(1H, br) |
| 78 | piperidin-1-yl | H | 0 | S | —NHCH₂CH₂—CH₂CH₃ | oily matter | 492 | 0.91(3H, t), 1.40(4H, m), 1.55(6H, m), 2.37(4H, bs), 2.80(2H, t), 3.23(2H, s), 3.39(2H, br), 3.44(2H, s), 3.76(2H, d), 4.00(2H, t), 4.63(2H, d), 5.67(1H, m), 5.88(1H, m), 6.39(1H, br), 6.80(1H, dd), 6.90(3H, m), 7.21(1H, t) |
| 79 | piperidin-1-yl | H | 1 | O | —OCH₃ | 96.5–99.4 | 451 | 1.43(2H, m), 1.56(4H, m), 2.37(4H, br), 3.05(2H, m), 3.44(2H, s), 3.45(1H, d), 3.66(3H, s), 3.67(1H, d), 4.01(2H, t), 4.62(2H, d), 5.66(1H, m), 5.85(2H, m), 6.79(1H, d), 6.89(1H, s), 6.90(1H, d), 7.20(1H, t), 7.28(1H, br) |
| 80 | piperidin-1-yl | H | 1 | O | —OCH₂CH₂CH₃ | oily matter | 479 | 0.92(3H, t), 1.43(2H, m), 1.57(6H, m), 2.37(2H, br), 3.05(2H, m), 3.41(1H, d), 3.44(2H, s), 3.65(2H, m), 3.70(1H, d), 4.01(4H, m), 4.62(2H, d), 5.65(2H, m), 5.87(1H, m), 6.78(1H, d), 6.90(2H, m), 7.20(1H, br), 7.21(1H, t) |
| 81 | piperidin-1-yl | H | 1 | O | —OCH₂CH=CH₂ | 69.0–70.5 | 477 | 1.43(2H, m), 1.57(4H, m), 2.38(4H, br), 3.05(2H, m), 3.42(1H, d), 3.44(2H, s), 3.66(2H, m), 3.70(1H, d), 4.03(2H, t), 4.56(2H, d), 4.63(2H, d), 5.27(2H, m), 5.68(2H, m), 5.87(2H, m), 6.80(1H, d), 6.92(2H, m), 7.14(1H, br), 7.21(1H, t) |
| 82 | piperidin-1-yl | H | 1 | O | —O(CH₂)₇CH₃ | oily matter | 549 | 0.88(3H, t), 1.27(10H, br), 1.43(2H, m), 1.57(6H, m), 2.38(4H, br), 3.05(2H, m), 3.40(1H, d), 3.44(2H, s), 3.65(2H, m), 3.70(1H, d), 4.04(4H, m), 4.63(2H, d), 5.47(1H, t), 5.67(1H, m), 5.86(1H, m), 6.79(1H, d), 6.92(2H, m), 7.09(1H, t), 7.21(1H, t) |
| 83 | piperidin-1-yl | H | 1 | O | —OCH₂—(phenyl) | oily matter | 527 | 1.43(2H, m), 1.56(4H, m), 2.37(4H, br), 3.04(2H, m), 3.40(1H, d), 3.43(2H, s), 3.65(2H, m), 3.66(1H, d), 4.00(2H, t), 4.61(2H, d), 5.09(2H, s), 5.65(1H, m), 5.74(1H, br), 5.83(1H, m), 6.78(1H, d), 6.89(1H, d), 6.91(1H, s), 7.12(1H, br), 7.20(1H, t), 7.33(5H, s) |

EXAMPLE 75

(a) N-[4-3-(piperidinomethyl) phenoxy]-cis-2-butenyl]-2-[2-(ethoxycarbonylamino)ethylsulfinyl] acetamide

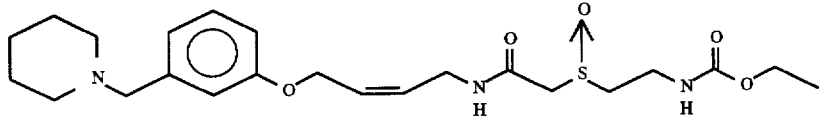

There was dissolved 1.64 g (0.0074 mol) of 2-[2-(ethoxycarbonylamino)ethylsulfinyl]acetic acid in 80 ml of 50% dimethylformamide-dichloromethane and added 1.13 g (0.0074 mol) of HOBt and 1.52 g (0.0074 mol) of DCC under cooling with ice, and the mixture was stirred for 30 minutes under cooling with ice. Thereto was added 1.91 g (0.0074 mol) of 4-[3-(piperidinomethyl)-phenoxy]-cis-2-butenylamine and the mixture was stirred for 18 hours at room temperature. The obtained precipitate was filtrated off, and the filtrate was washed with 5% aqueous solution of sodium hydroxide and with water successively, and dried over anhydrous sodium sulfate.

The solvent was removed under reduced pressure, and the residue was purified by silica gel column chromatography (chloroform:methanol=10:1). Then the obtained crystals were recrystallized from ethyl acetate-n-hexane (1:1) to give 1.3 g of the titled compound.

m.p.:64.7°–66.1° C.; MS(m/z):465(M$^+$); $^1$H-NMR (CDCL$_3$)δ: 1.24(3H, t), 1.43(2H, m), 1.57(4H, m), 2.38(4H, br), 3.05(2H, m), 3.41(1H, d), 3.44(2H, s), 3.65(2H, m), 3.70(1H, d), 4.03(2H, t), 4.11(2H, q), 4.63(2H, d), 5.53(1H, br), 5.65(1H, m), 5.68(1H, m), 6.79(1 H, dd), 6.90(2H, m), 7.10(1H, br), 7.21(1H, t)

(b) N-[4-[3-piperidinomethyl)-phenoxy]-cis-2-butenyl ]-2-[2-(ethoxycarbonylamino)ethylsulfinyl] acetamide hilbenzoate

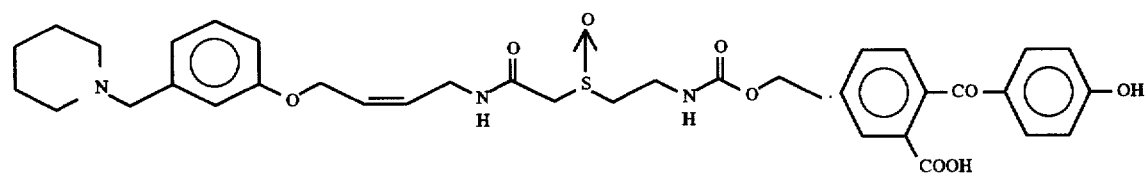

There were dissolved 9 g (0.0193 mol) of the acetamide obtained in the above step (a) and 4.68 g (0.0193 mol) or hibenzoic acid in 30 ml of ethanol and the mixture was stirred for 3 hours at room temperature. Thereto was added 120 ml of ethyl acetate, and when the deposit of crystals starts, the mixture was allowed to stand under cooling with ice. The deposited crystals were filtrated and dried, and then dissolved in 65 ml of ethanol. To the solution was added 360 m of ethyl acetate and the solution was allowed to stand at room temperature. When the deposit of crystals starts, the solution was allowed to stand further overnight in the refrigerator. The obtained crystals were filtrated to give 10 g of the hilbenzoate as white crystals.

m.p.:104.4°–107.7° C.; $^1$H-NMR(DMSO-d$_6$)δ: 1.20(3H, t), 1.39(2H, br), 1.51(4H, br), 2.56(4H, br), 2.95(1H, m), 3.05(1H, m), 3.46(2H, q), 3.61(1H, d), 3.67(2H, s), 3.71(1H, d), 3.84(2H, t), 4.03(2H, q), 4.61(2H, d), 5.60(1H, m), 5.70(1H, m), 6.80(2H, d), 6.85(2H, m), 6.97(1H, s), 7.22 (3H, m), 7.51(4H, m), 7.98(1H, dd) 8.41(1H, t) cl (c) N-[4-[3-(piperidinomethyl) phenoxy]-cis-2-butenyl]-2-[2-(ethoxycarbonylamino)ethylsulfinyl]acetamide fendizoate

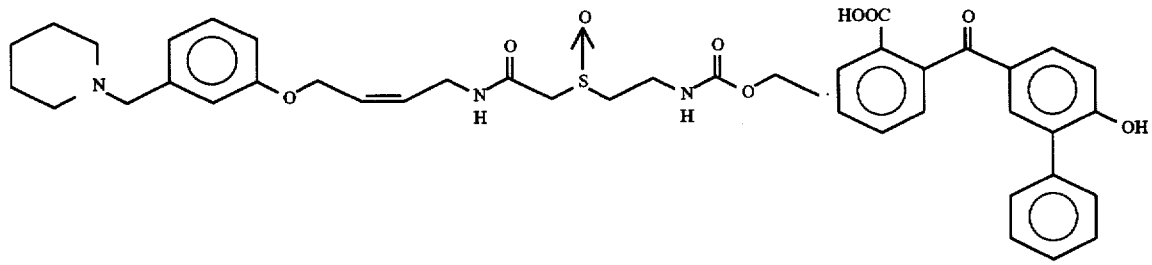

There were dissolved, at 50° C., 8.0 g (0.017 mol) of the acetamide obtained in the above step (a) and 5.47 g (0.017 mol) of fendizoic acid in 13 ml of ethanol and added 130 m of acetone and the mixture was allowed to cool. The deposited crystals were filtrated and recrystallized from 121 ml of a mixture of acetone-ethanol (10:1) to give 12.09 g of the fendizoate as white crystals.

m.p.:99.9°–102.6° C.; $^1$H-NMR(CDCl$_3$)δ: 1.15(5H, m), 1.42(4H, m), 2.16(4H, s), 2.91(2H, m), 3.61(8H, m), 4.02 (2H, q), 4.47(2H, m), 5.55(2H, m), 6.01(1H, m), 6.63(1H, d), 6.78(2H, m), 6.91(1H, s), 7.09(1H, t), 7.73(10H, m), 7.78(1H, s), 8.00(2H, m)

EXAMPLE 84

N-[3-[4-(piperidinomethyl) pyridyl-2-oxy]-propyl]-2-[2-(2-furoylamino)ethylthio]acetamide

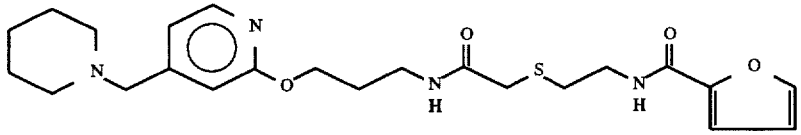

There was suspended 3.86 g (0.017 mol) of 2-[(2-furoylamino)ethylthio]acetic acid in 80 ml of dichloromethane and added 2.6 g (0.017 mol) of HOBt and 3.5 g (0.017 mol) of DCC under cooling with ice, and the mixture was stirred for 30 minutes under cooling with ice. Thereto was added 4.2 g (0.017 mol) of 3-[4-(piperidinomethyl) pyridyl-2-oxy]propylamine and the mixture was stirred for 18 hours at room temperature. The precipitate was filtrated off, and the filtrate was washed with 5% aqueous solution of sodium hydroxide and with water and dried over Glauber's salt. Then the solvent was removed under reduced pressure and the residue was purified by silica gel column chromatography (chloroform:methanol=10:1) to give 0.63 g of the titled compound as crystals.

m.p.:61.7°–62.7° C.; MS(m/z):460($M^+$); $^1$H-NMR (CDCl$_3$)δ: 1.45(2H, m), 1.60(4H, m), 2.00(2H, m), 2.39(4H, br), 2.81(2H, t), 3.28(2H, s), 3.43(2H, s), 3.45(2H, m), 3.65(2H, m), 4.40(2H, t), 6.48(1H, m), 6.78(1H, s), 6.88(1H, d), 6.89(1H, br), 7.10(1H, m), 7.40(1H, s), 7.41(1H, br), 8.06(1H, d)

According to the same manner as in Example 1 hydrochloride thereof was prepared.

EXAMPLE 85

N-[4-[4-(piperidinomethyl) pyridyl-2-oxy]-cis-2-butenyl]-2-[2-(3-furoylamino)ethylthio]acetamide

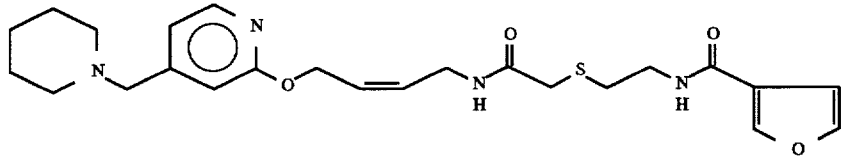

There was suspended 2.63 g (0.0115 mol) of 2-[(3-furoylamino)ethylthio]acetic acid in 60 ml of dichloromethane and added 1.76 g (0.0115 mol) of HOBt and 2.37 g (0.0115 mol) of DCC under cooling with ice, and the mixture was stirred for 30 minutes under cooling with ice. Thereto was added 3.0 g (0.0115 mol) of 4-[4-(piperidinomethyl)pyridyl-2-oxy]-cis-butenylamine and the mixture was stirred for 18 hours at room temperature. The precipitate was filtrated off, and the filtrate was washed with 10% aqueous solution of sodium 5 hydroxide and with saturated aqueous solution of sodium chloride and dried over Glauber's salt. Then the solvent was removed under reduced pressure and the residue was purified by silica gel column chromatography (chloroform:ethanol=10:1) to give 1.72 g of the titled compound as oily matter. MS(m/z):472 ($M^+$); $^1$H-NMR(CDCl$_3$)δ: 1.43(2H, m) 1.56(4H, m), 2.35 (4H, m), 2.79(2H, t), 3.27(2H, s), 3.39(2H, s), 3.58(2H, q), 4.03(2H, t), 4.91(2H, d), 5.65(1H, m), 5 83(1H, m), 6.73(1H, s), 6.80(1H, s), 6.87(1H, d), 7.38(1H, m), 7.73(1H, br), 8.01(3H, m)

According to the same manner as in Example 1 hydrochloride thereof was prepared.

EXAMPLE 86

N-[4-[4-(piperidinomethyl) pyridyl-2-oxy]-cis-2-butenyl]-2-[2-(N'-ethylureido)ethylthio]acetamide

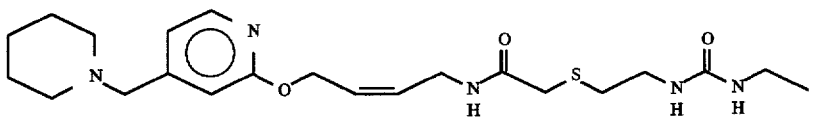

There was suspended 2.37 g (0.0115 mol) of 2-[(N'-ethylureido)ethylthio]acetic acid in 170 ml of dichloromethane and added 1.76 g (0.0115 mol) of HOBt and 2.37 g (0.0115 mol) of DCC under cooling with ice, and the mixture was stirred for 30 minutes under cooling with ice. Thereto was added 3.0 g (0.0115 mol) of 4-[4-(piperidinomethyl)pyridyl-2-oxy]-cis-butenylamine and the mixture was stirred for 18 hours at room temperature. The precipitate was filtrated off, and the filtrate was washed with 10% aqueous solution of sodium hydroxide and with saturated aqueous solution of sodium chloride and dried over Glauber's salt. Then the solvent was removed under reduced pressure and the residue was purified by silica gel column chromatography (chloroform:ethanol=10:1) to give 1.86 g of the titled compound as crystals.

m.p.: 79.9°–83.3° C.; MS(m/z):449($M^+$); $^1$H-NMR (CDCl$_3$)δ: 1.08(3H, t), 1.44(1H, m), 1.56(4H, m), 2.35(4H, m), 2.68(2H, t), 3.17(2H, m), 3.25(2H, s) , 3.36(2H, m), 3.40(2H, s), 4.03(2H, t), 4.91(2H, d), 5.64(2H, m), 5.84(1H, m), 6.01(1H, br), 6.73(1H, s), 6.87(1H, dd), 7.77(1H br), 8.03(1H, d)

According to the same manner as in Example 1 hydrochloride thereof was prepared.

EXAMPLE 87

N-[4-[4-(piperidinomethyl) pyridyl-2-oxy]-cis-2-butenyl]-2-[2-(N'-ethylthioureido)ethylthio] acetamide

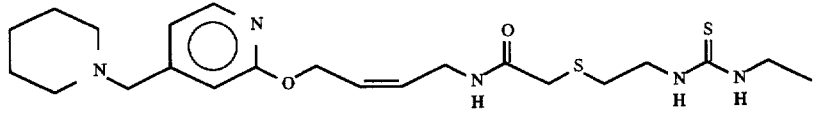

There was suspended 2.55 g (0.0115 mol) of 2-[(N'-ethylthioureido)ethylthio]acetic acid in 88 ml of dichloromethane and added 1.76 g (0.0115 mol) of HOBt and 2.37 g (0.0115 mol) of DCC under cooling with ice, and the mixture was stirred for 30 minutes under cooling with ice. Thereto was added 3.0 g (0.0115 mol) of 4-[4-(piperidinomethyl)pyridyl-2-oxy]-cis-butenylamine and stirred for 18 hours at room temperature. The precipitate was filtrated off, and the filtrate was washed with 10% aqueous solution of sodium hydroxide and with saturated aqueous solution of sodium chloride and dried over Glauber's salt. Then the solvent was removed under reduced pressure and the residue was purified by silica gel column chromatography (chloroform:ethanol=15:1) to give 3.9 g of the titled compound as oily matter.

MS(m/z):465(M$^+$); $^1$H-NMR(CDCl$_3$)δ: 1.19(3H, t), 1.44 (2H, m), 1.57(4H, m),), 2.36(4H, m), 2.81(2H, t), 3.28(2H, s), 3.41(2H, s), 3.43(2H, br), 3.76(3H q), 4.04(2H, t), 4.92(2H, d), 5.67(1H, m), 5.85(1H, m), 6.74(1H, s), 6.89 (1H, dd), 7.15(1H, br), 7.44(1H, br), 8.03(1H, d)

According to the same manner as in Example 1 hydrochloride thereof was prepared.

EXAMPLE 88

N-[4-[4-(piperidinomethyl) pyridyl-2-oxy]-cis-2-butenyl]-2-[2-(methoxycarbonylamino)ethylsulfinyl] -acetamide

There was suspended 1.6 g (0.0077 mol) of 2-[2-(methoxycarbonylamino)ethylsulfinyl]acetic acid in 80 ml of 50% DMF-dichloromethane and added 1.18 g (0.0077 mol) of HOBt and 1.59 g (0.0077 mol) of DCC under cooling with ice, and the mixture was stirred for 30 minutes under cooling with ice. Thereto was added 2.0 g (0.0077 mol) of 4-[4-(piperidinomethyl) pyridyl-2-oxy]-cis-butenylamine and stirred for 18 hours at room temperature. The precipitate was filtrated off, and the filtrate was washed with 5% aqueous solution of sodium hydroxide and with water and dried over Glauber's salt. Then the solvent was removed under reduced pressure and the residue was purified by silica gel column chromatography (chloroform:ethanol=10:1) to give 1.5 g of the titled compound as crystals.

m.p.:5.67°–58.8° C.; MS(m/z):452(M$^+$); $^1$H-NMR (CDCl$_3$)δ: 1.45(2H, m), 1.60(4H, m), 2.40(4H, m), 3.07(2H, m), 3.43(2H, s), 3.45(1H, d), 3.67(3H, s), 3.67(2H, m), 3.73(1H, d), 4.08(2H, t), 4.92(2H, d), 5.64(1H, br), 5.65(1H, m), 5.84(1H, m), 6.75(1H, s) 6.89(1H, d), 7.32(1H, t), 8.06(1H, d)

According to the same manner as in Example 1 hydrochloride thereof was prepared.

In the following, various kinds of acetamide derivatives were prepared according to the same manner as above. The melting point and the results of MS and NMR analysis, obtained as to the compounds of Examples are shown in Table 3.

TABLE 3

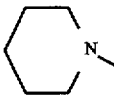

| Ex. | n | Y | R⁰ | m.p. °C. | MS(M⁺) | $^1$H—NMR(CDCl$_3$)δ: |
|---|---|---|---|---|---|---|
| 89 | 0 | O |  | 69.6–71.4 | 472 | 1.44(2H, m), 1.58(4H, m), 2.36(4H, m), 2.80(2H, t), 3.27(2H, s), 3.41(2H, s), 3.64(2H, q), 4.07(2H, t), 4.93(2H, d), 5.68(1H, m), 5.86(1H, m), 6.48(1H, dd), 6.74(1H, s), 6.88(1H, d), 6.97(1H, br), 7.12(2H, d), 7.44(1H, d), 8.05(1H, d) |
| 90 | 1 | O | 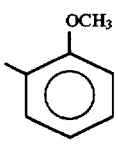 | 187 (decomp.) | 488 | 1.45(2H, m), 1.58(4H, m), 2.40(4H, m), 3.11(1H, m), 3.27(1H, m), 3.44(2H, s), 3.75(4H, m), 4.05(4H, m), 4.89(2H, d), 5.66(1H, m), 5.86(1H, m), 6.74(2H, m), 6.91(1H, dd), 7.43(1H, m), 8.04(2H, m) |
| 91 | 0 | O | OCH$_3$ 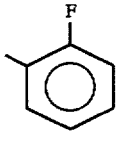 | oily matter | 512 | 1.43(2H, m), 1.57(4H, m), 2.35(4H, m), 2.81(2H, t), 3.29(2H, s), 3.39(2H, s), 3.67(2H, m), 3.98(3H, s), 4.07(2H, t), 4.91(2H, d), 5.65(1H, m), 5.80(1H, m), 6.72(1H, s), 6.86(1H, d), 6.98(1H, d), 7.06(1H, t), 7.23(1H, br), 7.44(1H, t), 8.05(1H, d), 8.19(1H, d), 8.26(1H, br) |
| 92 | 0 | O | F 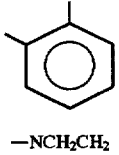 | oily matter | 500 | 1.45(2H, m), 1.60(4H, m), 2.36(2H, m), 2.83(2H, t), 3.28(2H, s), 3.39(2H, s), 3.70(2H, q), 4.08(2H, m), 4.92(2H, d), 5.67(1H, m), 5.84(1H, m), 6.72(1H, s), 6.87(1H, d), 7.18(4H, m), 7.45(1H, m), 8.06(2H, m) |
| 93 | 0 | O | NO$_2$ (phenyl) | 70.5–74.3 | 527 | 1.43(2H, m), 1.57(4H, m), 2.35(4H, m), 2.85(2H, t), 3.24(2H, s), 3.39(2H, s), 3.65(2H, q), 3.97(2H, t), 4.86(2H, d), 5.62(1H, m), 5.81(1H, m), 6.71(1H, s), 6.87(1H, d), 7.13(1H, br), 7.42(1H, br), 7.54(2H, m), 7.65(1H, m), 8.01(2H, m) |
| 94 | 0 | O | —NCH$_2$CH$_2$ H<br>—CH$_2$CH$_3$ | 73.5–74.8 | 477 | 0.88(3H, t), 1.34(6H, m), 1.57(4H, m), 2.35(4H, m), 2.68(2H, t), 3.13(2H, q), 3.24(2H, s), 3.36(2H, q), 3.40(2H, s), 4.04(2H, t), 4.92(2H, d), 5.41(1H, br), 5.67(1H, m), 5.84(2H, m), 6.73(1H, s), 6.88(1H, dd), 7.64(1H, br), 8.04(1H, d) |
| 95 | 0 | S | —NCH$_2$CH$_2$ H<br>—CH$_2$CH$_3$ | oily matter | 493 | 0.92(3H, t), 1.40(4H, m), 1.58(6H, m), 2.37(4H, m), 2.82(2H, t), 3.25(2H, s), 3.41(4H, s), 3.77(2H, m), 4.05(2H, m), 4.92(2H, d), 5.68(1H, m), 5.85(1H, m), 6.47(1H, br), 6.74(1H, s), 6.89(1H, d), 6.92(1H, br), 7.19(1H, br), 8.03(1H, d) |
| 96 | 0 | O | —OCH$_3$ | oily matter | 436 | 1.45(2H, m), 1.58(4H, m), 2.38(4H, m), 2.70(2H, t), 3.23(2H, s), 3.38(2H, q), 3.42(2H, s), 3.65(2H, s), 4.06(2H, t), 4.93(2H, d), 5.57(1H, br), 5.67(1H, m), 5.86(1H, m), 6.74(1H, s), 6.89(1H, dd), 7.20(1H, br), 8.05(1H, d) |
| 97 | 0 | O | —OCH$_2$CH$_3$ | oily matter | 450 | 1.22(3H, t), 1.45(2H, m), 1.58(4H, m), 2.37(4H, m), 2.70(2H, t), 3.23(2H, s), 3.37(2H, q), 3.42(2H, s), 4.08(4H, m), 4.93(2H, d), 5.55(1H, br), 5.68(1H, m) 5.86(1H, m), 6.74(1H, s), 6.88(1H, dd), 7.27(1H, br), 8.05(1H, d) |
| 98 | 0 | O | —OCH$_2$CH$_2$<br>—CH$_2$CH$_3$ | oily matter | 478 | 0.92(3H, t), 1.35(2H, m), 1.43(2H, m), 1.59(4H, m), 2.38(4H, m), 2.70(2H, t), 3.23(2H, s), 3.38(2H, q), 3.41(2H, s), 4.05(4H, m), 4.93(2H, d), 5.37(1H, br), 5.68(1H, m), 5.87(1H, m), 6.74(1H, s), 6.88(1H, d), 7.15(1H, br), 8.05(1H, d) |
| 99 | 0 | O | —OCH$_2$CH$_2$<br>—OCH$_3$ | oily matter | 480 | 1.45(2H, m), 1.57(4H, m), 2.37(4H, m), 2.70(2H, t), 3.23(2H, s), 3.38(3H, s), 3.40(2H, m), 3.41(2H, s), 4.07(2H, t), 4.20(2H, m), 4.93(2H, d), 5.39(1H, br), 5.70(1H, m), 5.88(1H, m), 6.74(1H, s), 6.88(1H, d), 7.09(1H, br), 8.05(1H, d) |
| 100 | 1 | O | —OCH$_2$CH$_3$ | oily matter | 466 | 1.24(3H, t), 1.44(2H, m), 1.59(4H, m), 2.39(4H, m), 3.07(2H, m), 3.42(2H, s), 3.44(1H, d), 3.66(2H, m), 3.73(1H, d), 4.10(4H, m), 4.92(2H, d), 5.56(1H, br), 5.70(1H, m), 5.85(1H, m), 6.74(1H, s), 6.89(1H, d), 7.33(1H, br), 8.06(1H, d) |
| 101 | 1 | O | —OCH$_2$CH$_2$ | 89.7– | 494 | 0.92(3H, t), 1.42(4H, m), 1.56(6H, m), 2.37(4H, m), |

TABLE 3-continued

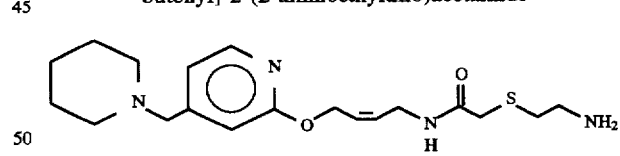

| Ex. | n | Y | R⁰ | m.p. °C. | MS(M⁺) | ¹H—NMR(CDCl₃)δ: |
|---|---|---|---|---|---|---|
| | | | —CH₂CH₃ | 91.0 | | 3.06(2H, m), 3.40(2H, s), 3.43(1H, d), 3.66(2H, m), 3.71(1H, d), 4.07(4H, m), 4.91(2H, d), 5.52(1H, t), 5.65(1H, m), 5.86(1H, m), 6.73(1H, s), 6.87(1H, d), 7.29(1H, br), 8.05(1H, d) |
| 102 | 0 | =N—CN | —CH₃ | oily matter | 444 | 1.44(2H, m), 1.57(4H, m), 2.33(3H, s), 2.35(4H, m), 2.81(2H, t), 3.26(2H, s), 3.41(2H, s), 3.52(2H, m), 4.05(2H, t), 4.85(2H, d), 5.70(1H, m), 5.86(1H, m), 6.74(1H, s), 6.89(1H, d), 7.35(1H, br), 8.02(1H, d), 8.46(1H, br) |

EXAMPLE 103

N-[3-[3-(piperidinomethyl)phenoxy]propyl]-2-(2-aminoethylthio)acetamide

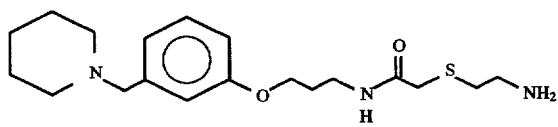

There was dissolved 15.0 g (0.0604 mol) of 3-[3-(piperidinomethyl)phenoxy]propylamine in 150 ml of dichloromethane and added dropwise 6. 82 g (0.0604 mol) of chloroacetyl chloride under cooling with ice. After dropping, the mixture was stirred for 3.5 hours under cooling with ice and then the solvent was removed under reduced pressure. The residue was dissolved in 150 ml of ethanol and this solution was added to a solution which was prepared by adding 4.65 g (0.0604 mol) of 2-aminoethanethiol to a solution of 3.06 g (0.1329 mol) of sodium 150 ml of ethanol and stirring for 30 minutes at room temperature, and the obtained mixture was refluxed with heating for 3 hours. After being allowed to cool at room temperature, the precipitate was filtrated off, and the solvent was removed under reduced pressure. The obtained residue was dissolved in ethyl acetate and washed with water, and dried over Glauber's salt. Then the solvent was removed under reduced pressure to give 20.4 g of the titled compound as oily matter.

MS(m/z):365(M⁺); ¹H-NMR(CDCl₃ )δ: 1.42(2H, m), 1.57(4H, m), 1.97(2H, br), 2.37(4H, br), 2.78(2H, m), 2.94 (2.94H, t), 3.26(2 1H, s), 3.51(2H, m) , 4.03(2H, m), 6.78(1H, m), 6.88(2H, m), 7.19(1H, m)

EXAMPLE 104

N-[4-[3-(piperidinomethyl)phenoxy]-cis-2-butenyl]-2-(2-aminoethylthio)acetamide

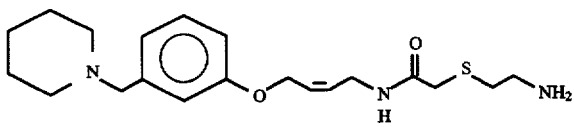

There was dissolved 15.0 g (0.0577 mol) of 4-[3-(piperidinomethyl)phenoxy]-cis-butenylamine in 150 ml of dichloromethane and added dropwise 6.52 g (0.0577 mol) of chloroacetyl chloride under cooling with ice. After dropping, the mixture was stirred for 3.5 hours under cooling with ice and then the solvent was removed under reduced pressure. The residue was dissolved in 150 ml of ethanol and this solution was added to a solution which was prepared by adding 4.44 g (0.0577 mol) of 2-aminoethanethiol to a solution of 2.65 g (0.115 mol) of sodium in 150 ml of ethanol and stirring for 30 minutes at room temperature, and the obtained mixture was refluxed with heating for 1 hour. After being allowed to cool at room temperature, the precipitate was filtrated off, and the solvent was removed under reduced pressure. The obtained residue was dissolved in ethyl acetate and washed with water, and dried over Glauber's salt. Then the solvent was removed under reduced pressure to give 18.5 g of the titled compound as oily matter.

MS(m/z):377(M⁺); ¹H-NMR(CDCl₃)δ: 1.43(2H, m), 1.57 (4H, m) , 2.04(2H, br), 2.38(4H, br), 2.63(2H, t), 2.89(2H, t), 3.22(2H, s), 3.44(2H, s), 4.01(2H, t), 4.64 (2H, d), 5.71(1H, m), 5.86(1H, m), 6.80(1H, dd), 6.91(1H, d), 6.92 (1H, s), 7.21(1H, t), 7.37(1H, br)

EXAMPLE 105

N-[4-[4-(piperidinomethyl)pyridyl-2-oxy]-cis-2-butenyl]-2-(2-aminoethylthio)acetamide There was dissolved 1.5 g (0.0057 mol) of 4-|4-(piperidinomethyl)pyridyl-2-oxy]-cis-2-butenylamine in 30 ml of dichloromethane and added dropwise 0.71 g (0.0063 mol) of chloroacetyl chloride under cooling with ice. After dropping, the mixture was stirred for 30 minutes under cooling with ice and for 1 hour at room temperature, and then the solvent was removed under reduced pressure. The residue was dissolved in 20 ml of ethanol and this solution was added to a solution which was prepared by adding 0.44 g (0.0057 mol) of 2-aminoethanethiol to a solution of 0.26 g (0.0114 mol) of sodium in 30 ml of ethanol and stirring for 30 minutes at room temperature, and the obtained mixture was refluxed with heating for 1 hour. The precipitate was filtrated off, and the solvent was removed under reduced pressure. The residue was dissolved in chloroform and washed with water, and dried over Glauber's salt. Then the solvent was removed under reduced pressure, and the residue was purified by silica gel column chromatography (chloroform:methanol:28% aqueous ammonia=30:3:0.1) to give 1.2 g of the titled compound as oily matter.

MS(m/z):378 (M$^+$); $^1$H-NMR(CDCl$_3$)δ: 1.44(2H, m), 1.58(6H, m) 2.37(4H, m), 2.66(2H, m), 2.83(2H, m)), 3.23 (2H, s), 3.41(2H, s), 4.06(2H, m), 4.93(2H, d), 5.67(1H, m), 5.87(1H, m), 6.74(1H, s), 6.88(1H, d), 7.38(1H, br), 8.06 (1H, d)

EXAMPLE 106

Ethyl 2-[2-(ethoxycarbonylamino)ethylthio]-acetate

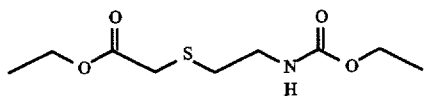

There was suspended 50 g (0.65 mol) or 2-aminoethanethiol in 660 ml of ethanol and, under cooling with ice, added 65.6 g (0.65 mol) of triethylamine and added dropwise 79.6 g (0.65 mol) of ethyl chloroacetate, and then the mixture was stirred for 1 hour under cooling with ice. Then thereto was added 65.6 g (0.65 mol) of triethylamine and added dropwise 70.6 g (0.65 mol) of ethyl chloroformate, and the mixture was stirred for 1 hour under cooling with ice, and further for 18 hours at room temperature. After the solvent was removed under reduced pressure, the residue was dissolved in chloroform and washed with water, and dried over anhydrous sodium sulfate. Then the solvent was removed under reduced pressure to give 137 g of the titled compound as oily matter.

MS(m/z):235(M$^+$); $^1$H-NMR(CDCl$_3$)δ: 1.24(3H, t), 1.29 (3H, t), 2.79(2H, t), 3.25(2H, s), 3.40(2H, m), 4.12(2H, q), 4.20(2H, q), 5.35(1H, br)

EXAMPLE 107

Ethyl 2-[2-(ethoxycarbonylamino)ethylsulfinyl]-acetate

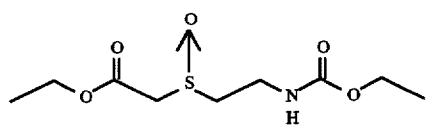

There was dissolved 149.7 g (0.7 mol) of sodium metaperiodate in 1400 ml of water, and thereto was added dropwise a solution of 164.5 g (0.7 mol) of ethyl 2-[2-(ethoxycarbonylamino)ethylthio]acetate in 125 ml of methanol under cooling with ice. After dropping the mixture was stirred for, hours under cooling with ice. The precipitate was removed by filtration and washed with water and with chloroform, successively. The filtrate was extracted with chloroform and dried over anhydrous sodium sulfate. Then the solvent was removed under reduced pressure to give 138.6 g of white solid. The solid was recrystallized from ethanol-n-hexane (1:4) to give 113.5 g of the titled compound.

m.p.:73.8°-77.0° C.; MS(m/z)252(M$^+$+1); $^1$H-NMR (CDCl$_3$)δ: 1.24(3H, t), 1.31(3H, t), 3.04(1H, m), 3.20(1H, m), 3.71(2H, m), 3.76(2H, s), 4.12(2H, q), 4.26(2H, q), 5.55(1H, br)

EXAMPLE 108

2-[2-(ethoxycarbonylamino)ethylsulfinyl]acetic acid

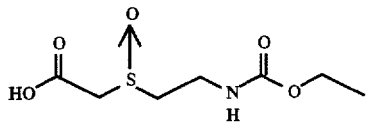

There was added 30 g (0.12 mol) of ethyl 2-[2-(ethoxycarbonylamino)ethylsulfinyl]acetate to a solution of 9.56 g of sodium hydroxide dissolved in 120 ml of water, and the mixture was stirred for 2 hours at room temperature and washed with ethyl acetate. The alkaline phase was separated and acidified with conc. HCl under cooling with ice, and the solvent was removed under reduced pressure. The residue was dissolved in ethanol and the insoluble substance was removed by filtration. The filtrate was removed under reduced pressure, and the residue was dissolved in chloroform and dried over anhydrous sodium sulfate. Then the solvent was removed under reduced pressure to give 18.36 g of white solid. The solid was recrystallized from ethanol-n-hexane (1:1) to give 15.0 g of the titled compound.

m.p.:93.1°-94.1° C. $^1$H-NMR(DMSO-d$_6$)δ: 1.17(3H, t), 2.96(2H, m), 3.38(2H, m), 3.68(1H, d), 3.93(1H, d), 4.00 (2H, q), 7.34(1H, br)

Test Example

With respect to anti-ulcer effect of the compounds having the general formula (I), there were carried out a test of ulcer induced by pylorus-ligation, which ulcer is induced mainly due to offensive factors; a test of ulcer induced by hydrochloric acid/ethanol, which ulcer is induced mainly due to defensive factors such as mucosal blood flow and mucus; and a test of ulcer induced by a stress of restraint plus water-immersion, which ulcer is induced due to both of offensive and defensive factors. Further, there were carried out a test of ulcer induced by acetic acid as a chronic ulcer model and a test of cure-prolonged ulcer induced by acetic acid. Also, there was examined an activity of increasing gastric mucosal blood flow, which activity brings about acceleration of regeneration of the gastric mucosa. As test compounds, hydrochloride salts were used.

The test methods and results thereof are shown in the followings.

[Test of ulcer induced by pylorus-ligation]

The pylorus of a wistar male rat weighing 230 to 250 g, which had fasted for 48 hours, was ligated under ether-anesthesia, according to a usual method. After 14 hours, the animal was sacrificed by ether and the stomach was taken out therefrom.

The area of the ulcer generated on the fore-stomach was measured and the total area of the ulcer per rat was classified into the following six grades to give ulcer coefficients (Table 4).

TABLE 4

| Area of ulcer (mm$^2$) | 0 | ≦10 | ≦20 | ≦30 | ≦40 | 40 < or perforation |
|---|---|---|---|---|---|---|
| Ulcer coefficient | 0 | 1 | 2 | 3 | 4 | 5 |

As test compounds, there were used the compounds of the present invention and, as comparative compounds, cimetidine, famotidine and a compound (hereinafter, referred to as FRG-8813):

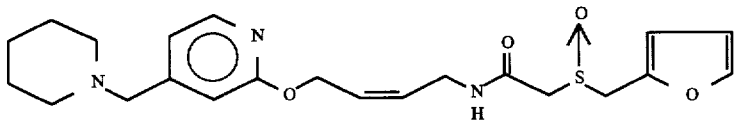

which is described in Example 2 of Japanese Unexamined Patent Publication No. 225371/1988, U.S. Pat. No. 4,912,101 and U.S. Pat. No. 4,977,267. Each of them was suspended in 0.5% methylcellulose solution and administered in the duodenum immediately after ligating the pylorus, in a dose of 100 mg/kg (body weight), respectively. To control group, only the medium for the medicament solution was administered in an amount of 0.25 ml/100 g (body weight).

The obtained results were subjected to the following formula to calculate a percentage of inhibition of ulcer formation. Six rats were used in each group for the test:

Percentage of inhibition of ulcer formation (%) =

$$\left(1 - \frac{\text{Ulcer coefficient of test compound - administered group}}{\text{Ulcer coefficient of control group}}\right) \times 100$$

The results are shown in Table 5.

TABLE 5

| Test compound | Percentage of inhibition of ulcer formation (%) |
|---|---|
| Example 4 | 73 |
| Example 5 | 57 |
| Example 6 | 67 |
| Example 8 | 50 |
| Example 10 | 73 |
| Example 11 | 55 |
| Example 12 | 77 |
| Example 13 | 68 |
| Example 14 | 63 |
| Example 15 | 68 |
| Example 16 | 70 |
| Example 44 | 57 |
| Example 48 | 95 |
| Example 73 | 60 |
| Example 75 | 96 |
| Example 79 | 57 |
| Example 81 | 76 |
| Example 91 | 69 |
| Example 95 | 73 |
| Comparative compound (cimetidine) | 27 |
| Comparative compound (famotidine) | 70 |
| Comparative compound (FRG-8813) | 27 |

From Table 5 it is proved that the compounds of the present invention show potent anti-ulcer effect against the ulcer induced by pylorus-ligation.

[Test of ulcer induced by hydrochloric acid/ethanol]

To a wistar male rat weighing 220 to 240 g, which had fasted and thirsted for 24 hours, was orally administered 15 mM hydrochloric acid/70% ethanol solution in an amount of 5 ml/kg (body weight). After 1 hour, the animal was sacrificed by dislocating the cervical vertebrae and the stomach was taken out therefrom. The length of the ulcer generated on the glandular stomach was measured and the total thereof was regarded as the ulcer coefficient (mm).

As test compounds, there were used the compounds of the present invention and, as comparative compounds, cimetidine, famotidine and FRG-8813. Each of them was suspended in 0.5% methylcellulose solution, and administered orally 30 minutes before the administration of hydrochloric acid/ethanol in a dose of 30 mg/kg (body weight) in case of the compounds of the present invention and FRG-8813, and in a dose of 100 mg/kg (body weight) in case of cimetidine and famotidine. To control group, only the medium for the medicament solution was orally administered in an amount of 0.5 ml/100 g (body weight), 30 minutes before the administration of hydrochloric acid/ethanol.

The obtained results were subjected to the same formula as in the test of ulcer induced by pylorus-ligation, to calculate a percentage of inhibition of ulcer formation. Six rats were used in each group for the test.

The results are shown in Table 6.

From Table 6, it is proved that the compounds of the present invention show potent anti-ulcer effect against the ulcer induced by hydrochloric acid/ethanol.

TABLE 6

| Test compound | Percentage of inhibition of ulcer formation (%) |
|---|---|
| Example 4 | 97 |
| Example 5 | 97 |
| Example 6 | 61 |
| Example 8 | 90 |
| Example 10 | 89 |
| Example 11 | 51 |
| Example 12 | 68 |
| Example 13 | 69 |
| Example 14 | 77 |
| Example 15 | 60 |
| Example 16 | 62 |
| Example 44 | 83 |
| Example 48 | 73 |
| Example 73 | 67 |
| Example 75 | 82 |
| Example 79 | 78 |
| Example 81 | 69 |
| Example 91 | 87 |
| Example 95 | 72 |
| Comparative compound (cimetidine) | 7 |
| Comparative compound (famotidine) | 34 |
| Comparative compound (FRG-8813) | 70 |

[Test of ulcer induced by a stress of restraint plus water-immersion]

A ddY male mouse weighing 20 to 25 g, which had fasted for 18 hours, was put into a stress cage, and was loaded with a stress by immersing it in a water tank at 23° C., to a level of a xiphoid. After 7 hours, the animal was sacrificed by dislocating the cervical vertebrae and the stomach was taken out therefrom. The length of the ulcer generated on the glandular stomach was measured and the total thereof was regarded as the ulcer coefficient (mm).

As test compounds, there were used the compounds of the present invention and, as comparative compounds, cimetidine, famotidine and FRG-8813. Each of them was suspended in 0.5% methylcellulose solution, and administered orally 15 minutes before the load of the stress, in a dose of 30 mg/kg (body weight) in case of the compounds of the present invention, famotidine and FRG-8813, and in a dose of 100 mg/kg (body weight) in case of cimetidine. To control group, only the medium for the medicament solution was orally administered in an amount of 0.1 ml/10 g (body weight) 15 minutes before the load of the stress.

The obtained results were subjected to the same formula as in the test of ulcer induced by pylorus-ligation, to calculate a percentage of inhibition of ulcer formation. Six rats were used in each group for the test.

The results are shown in Table 7.

From Table 7, it is proved that the compounds of the present invention show potent anti-ulcer effect against the ulcer induced by the stress of restraint plus water-immersion.

TABLE 7

| Test compound | Percentage of inhibition of ulcer formation (%) |
|---|---|
| Example 4 | 75 |
| Example 5 | 93 |
| Example 6 | 88 |
| Example 8 | 93 |
| Example 10 | 73 |
| Example 11 | 70 |
| Example 12 | 68 |
| Example 13 | 89 |
| Example 14 | 91 |
| Example 15 | 98 |
| Example 16 | 74 |
| Example 44 | 77 |
| Example 48 | 100 |
| Example 73 | 69 |
| Example 75 | 87 |
| Example 79 | 67 |
| Example 81 | 73 |
| Example 91 | 83 |
| Example 95 | 71 |
| Comparative compound (cimetidine) | 61 |
| Comparative compound (famotidine) | 100 |
| Comparative compound (FRG-8813) | 85 |

[Test of ulcer induced by acetic acid]

Into the junction of the glandular stomach and the antrum, of a wistar male rat weighing 220 to 240 g, was injected subserosally 30 μl of 20% acetic acid to generate an ulcer induced by acetic acid. As test compounds, there were used the compound of the present invention and, as comparative compounds, FRG-8813 and famotidine. Each of them was suspended in 0.5% methylcellulose solution, and administered orally in a dose of 15 mg/kg, twice a day (in the morning and in the evening) from 2 days after the generation of the ulcer for 8 days, respectively. The animal was sacrificed by ether on the day after the last administration, and the stomach was taken out therefrom. The area of the ulcer was measured.

The obtained results were subjected to the following formula to calculate a percentage of improvement for curing ulcer. To control group, only the medium for the medicament solution was administered in an amount of 0.5 ml/100 g (body weight). Twenty rats were used in each group for the test.

Percentage of improvement for curing ulcer (%) =

$$\left(1 - \frac{\text{Ulcer coefficient of test compound - administered group}}{\text{Ulcer coefficient of control group}}\right) \times 100$$

The results are shown in Table 8.

From Table 8, it is prove that the compounds of the present invention show accelerating effect for curing the ulcer induced by acetic acid.

TABLE 8

| Test compound | Percentage of improvement for curing ulcer (%) |
|---|---|
| Example 75 | 24 |
| FRG-8813 | 12 |
| Famotidine | 7 |

[Test if cure-prolonged ulcer induced by acetic acid]

Into the junction of the glandular stomach and the antrum, of a wistar male rat weighing 220 to 240 g, was injected subserosally 30 μl of 20% acetic acid to generate an ulcer induced by acetic acid. From 2 days after the generation of the ulcer, indomethacin was injected subcutaneously in the regions of back of the rat in a dose of 1 mg/kg, once a day for 13 days to prolong the cure of the ulcer induced by acetic acid.

As test compounds, there were used the compound of the present invention and, as comparative compounds, FRG-8813 and famotidine. Each of them was suspended in 0.5% methylcellulose solution, and administered orally in a dose of 50 mg/kg, twice a day (in the morning and in the evening) from 13 days, respectively. The animal was sacrificed by ether on the day after the last administration, and the stomach was taken out therefrom. The area of the ulcer was measured. The obtained results were subjected to the following formula to calculate a group, only the medium of the medicament solution was administered in an amount of 0.5 ml/100 g (body weight). Twenty rats were used in each group for the test.

Percentage of improvement for curing ulcer (%) =

$$\left(1 - \frac{\text{Ulcer coefficient of test compound - administered group}}{\text{Ulcer coefficient of control group}}\right) \times 100$$

The results are shown in Table 9.

From Table 9, it is proved that the compounds of the present invention show potent accelerating effect for curing the cure-prolonged ulcer by acetic acid.

TABLE 9

| Test compound | Percentage of improvement for curing ulcer (%) |
|---|---|
| Example 75 | 49 |
| FRG-8813 | -5 |
| Famotidine | 26 |

[Activity of increasing gastric mucosal blood flow]

An amount of the mucosal blood flow in the body of the stomach of a wistar male rat weighing 220 to 240 g under urethane-anesthesia was measured by means of a laser doppler blood flow meter. As test compounds, there were used the compound FRG-8813. Each of them was intravenously administered in a dose of 220 μg/kg. A percentage of increase of the blood flow was calculated 60 minutes after the administration. Five rats were used for each group for the test.

The results are shown in Table 10.

From Table 10, it is proved that the compounds of the present invention increase the amount of the gastric mucosal blood flow.

TABLE 10

| Test compound | Percentage of increase of blood flow (%) |
|---|---|
| Example 75 | 15 |
| FRG-8813 | 3 |

[Toxicity test]

Five wistar male rats weighing about 150 g were used in each group, and the compound obtained in Example 4, 5, 6, 8, 10, 11, 12, 13, 14, 15, 16, 44, 48, 73, 75, 79, 81, 91 or 95 was orally administered as a test compound.

As to all the test compounds, no rat died in a dose of up to 1000 ml/kg.

Preparation example 1

Tablets including 100 ml of an effective ingredient per tablet were prepared according to the following formulation.

| (Ingredient) | (mg) |
|---|---|
| Compound obtained in Example 4 | 100 |
| Crystalline cellulose | 50 |
| Calcium carboxymethylcellulose | 10 |
| Sodium laurylsulfate | 1 |
| Methylcellulose | 3 |
| Calcium stearate | 4 |

Preparation Example 2

Capsules were prepared by filling 200 ml of the mixed ingredients including 100 ml of an effective ingredient per capsule according to the following formulation.

| (Ingredient) | (mg) |
|---|---|
| Compound obtained in Example 4 | 100 |
| Lactose | 50 |
| Corn starch | 40 |
| Crystalline cellulose | 8 |
| Calcium stearate | 2 |

We claim:

1. An aminoethanethiol derivative having the formula (XX):

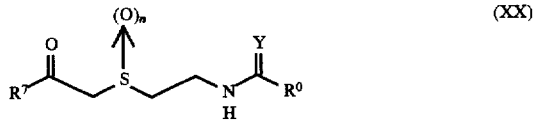

wherein $R^7$ is hydroxyl group, a $C_{1-7}$ alkoxy group, or a phenoxy group which may be substituted by a nitro of fluoro group, n is 0 or 1, Y is oxygen atom, sulfur atom or =N—CN, and $R^0$ is —$OR^6$, wherein $R^6$ is hydrogen atom; a $C_{1-8}$ alkyl group; a $C_{2-6}$ alkenyl group; a $C_{2-6}$ alkynyl group; a $C_{1-4}$ alkoxy $C_{1-7}$ alkyl group; a $C_{1-5}$ acyloxy $C_{1-7}$ alkyl group; a $C_{7-16}$ aralkyl group; a phenyl or a heterocyclic group which may be substituted by a $C_{1-7}$ alkyl group, a halogen atom, a $C_{1-4}$ alkoxy group, nitro group, trifluoromethyl group, amino group, cyano group, carboxyl group or acetyl group; a $C_{1-7}$ alkyl group substituted by a heterocycle.

* * * * *